US012606536B2

(12) United States Patent
Domb et al.

(10) Patent No.: US 12,606,536 B2
(45) Date of Patent: Apr. 21, 2026

(54) BIOACTIVE PHENOLATE IONIC COMPLEXES

(71) Applicants: YISSUM RESEARCH DEVELOPMENT COMPANY OF THE HEBREW UNIVERSITY OF JERUSALEM LTD., Jerusalem (IL); HADASIT MEDICAL RESEARCH SERVICES & DEVELOPMENT LIMITED, Jerusalem (IL)

(72) Inventors: Abraham Jacob Domb, Jerusalem (IL); Noam Steinman, Jerusalem (IL); Yakir Rottenberg, Elazar (IL)

(73) Assignees: YISSUM RESEARCH DEVELOPMENT COMPANY OF THE HEBREW UNIVERSITY OF JERUSALEM LTD., Jerusalem (IL); HADASIT MEDICAL RESEARCH SERVICES & DEVELOPMENT LIMITED, Jerusalem (IL)

( * ) Notice: Subject to any disclaimer, the term of this patent is extended or adjusted under 35 U.S.C. 154(b) by 724 days.

(21) Appl. No.: 17/996,694

(22) PCT Filed: Apr. 21, 2021

(86) PCT No.: PCT/IL2021/050450

§ 371 (c)(1),
(2) Date: Oct. 20, 2022

(87) PCT Pub. No.: WO2021/214762

PCT Pub. Date: Oct. 28, 2021

(65) Prior Publication Data

US 2023/0234934 A1 Jul. 27, 2023

Related U.S. Application Data

(60) Provisional application No. 62/704,121, filed on Apr. 22, 2020.

(51) Int. Cl.
*C07D 311/80* (2006.01)
*C07C 39/23* (2006.01)
*C07C 39/235* (2006.01)

(52) U.S. Cl.
CPC .......... *C07D 311/80* (2013.01); *C07C 39/235* (2013.01); *C07C 2601/16* (2017.05)

(58) Field of Classification Search
CPC .. C07D 311/80; C07C 39/235; C07C 2601/16
See application file for complete search history.

(56) References Cited

U.S. PATENT DOCUMENTS

| | | | |
|---|---|---|---|
| 1,917,749 | A | 7/1933 | Britton |
| 2,353,725 | A | 7/1944 | Gump |
| 2,480,823 | A | 9/1949 | Morris et al. |
| 2019/0144367 | A1 | 5/2019 | Andrews et al. |

FOREIGN PATENT DOCUMENTS

| | | | |
|---|---|---|---|
| FR | 1.026.965 | A | 5/1953 |
| FR | 1.198.735 | A | 12/1959 |
| WO | 2007/003200 | A2 | 1/2007 |
| WO | 2008/109385 | A2 | 9/2008 |
| WO | 2016/127111 | A1 | 8/2016 |
| WO | 2021/041637 | A1 | 3/2021 |

OTHER PUBLICATIONS

Dvorackova, et al., Effects of Extraction Methods on the Phenolic Compounds Contents and Antioxidant Capacities of Cinnamon Extracts, Food Sci. Biotechnol, 24(4):1201-1207 (2015).
Hoshino, et al., Selective Synthesis and Biological Evaluation of Sulfate-Conjugated Resveratrol Metabolites, J. Med. Chem., 53(13):5033-5043 (2010).

*Primary Examiner* — Sikarl A Witherspoon
(74) *Attorney, Agent, or Firm* — FISHERBROYLES, LLP; Roger L. Browdy

(57) ABSTRACT

The invention provides an isolated material, or a phenolate form of at least one phenol-containing active material, wherein the isolated material comprises one or more phenolate species and a counter ion (a cation) in the form of a metal salt, a phosphonium or an ammonium.

21 Claims, No Drawings

BIOACTIVE PHENOLATE IONIC COMPLEXES

TECHNOLOGICAL FIELD

The invention generally concerns novel ionic—metal, phosphonium and ammonium phenolates of active agent and uses thereof.

BACKGROUND

A great variety of bioactive materials containing phenol groups are found in nature and play an integral role in human diet. Phenol-containing materials are also found in several important synthetic and natural drugs, for example apomorphine, estron, estradiol, propopfol, O-phenyl phenol, L-Dopa, doxorubicin, cannabinoids active molecules such as tetrahydrocannabidiol (THC) and Cannabidiol (CBD) and peptide or protein molecules containing tyrosine. Another example is salcaprozate sodium (SNAC), an oral absorption enhancer for peptides and vitamins, natural and modified polyphenols such as curcumin, flavone, flavanol, anthocyanin, gallic acid, caffeic acid, thymol, salicylic acid, hydroxystilbenes, selariscinin and more.

It is well known that phenolic substances, such as ortho- or para-catechol, possess low chemical stability in aqueous solutions due to oxidation or reaction with aldehydes and nucleophiles. It is further known that these phenolic drugs often have low solubility and bioavailability. Oral delivery is thus limited, leading to the production of pro-drug substitutes for oral administration. In some cases, there is a need for reducing or enhancing penetration through skin, such as sunscreen molecules which can be achieved by phenolate salt formation.

International Publication No. WO2016/127111 teaches adducts of CBD and lanthanide metal complexed with three heptafluoro alkyl ligands, where the OH of the CBD is not converted to a phenolate anion.

GENERAL DESCRIPTION

To overcome many of the difficulties associated with phenol-containing active materials, the inventors of the technology disclosed herein have transformed these active materials into pro-drug entities in a form of salts, endowing them with:

- improved chemical stability;
- reduced sensitivity to oxidation; and
- improved physical properties, such as improved water solubility, ease of crystallization, purity and others.

By transforming the compounds into their respective salts, the inventors have allowed the formation of multi-drug vehicles comprising one or more, same or different, drug entities within a single dosage form. In other words, a single cation may be associated with two or more, same or different, drug entities that can be administered or used as a unit.

Thus, in most general terms, the invention provides an isolated material, or a phenolate form of at least one phenol-containing active material, wherein the isolated material comprises one or more phenolate species and a counter ion (a cation) in the form of a metal salt, a phosphonium or an ammonium, and wherein the active material is not phenol ($C_6H_6O$), methylphenol, bromophenol, dibromophenol, tribromophenol, pentachlorophenol, bisphenol A, tetrabromobisphenol A, resorcinol, hydroquinone, hydroquinone or naphthol. The one or more phenolate species are presented in a form that enables increased stability, efficient dissolution in aqueous media, more efficient delivery and improved bioavailability. As each of the material products of the invention dissociates into the phenol-containing compound and the metal cation, the materials of the invention must not be metal adducts nor metal coordination compounds, as known in the art.

Materials of the invention are regarded as isolated materials. The term “isolated” means that the material is neither an accidental material nor an intermediate material that remains in the soup or medium in which it is produced and is not isolated. The isolated material is thus of high purity. The purity may be 100%, or more than 80%. The purity may also depend on the purity needed for each of the uses or utilities for which yhe material is intended. In some embodiments, the isolated material of the invention is a pharmaceutical grade, a cosmetically grade or an agricultural grade, as defined in the art.

Materials that are not isolated do not form part of the present invention.

Materials of the invention are water soluble forms of lipophilic or water insoluble active materials. This water-soluble form is ionic in which the counterion is as defined hereinbelow. Without wishing to be bound by theory, materials of the invention are converted in the body, following administration, into the respective active species, namely active phenol compounds or may remain ionized. For example, where the active material is a cannabinoid, it is presented in a material of the invention in its ionized phenolate form which, in the body, may be converted back to the non-ionized form.

As known in the art, a phenol-containing active material is a compound having an aromatic hydrocarbon group (benzene ring, phenyl ring, a naphthyl group, a fused aromatic ring and others) having one or more hydroxyl groups (—OH) bonded to one or more of the ring carbon atoms. The phenol-containing active material is typically a bioactive compound used in medicine, cosmetics, veterinary or agriculture. The active material may be synthetic or phyto-derived. The salt form is a metal salt form, an ammonium salt form, a nitronium salt form or a phosphonium salt form. The metal salt form contains a metal cation and a phenolate compound. In other words, the bond associating the metal cation and the charged oxygen atom of the phenolate compound is ionic of the sorts typically associating cations and anions. The number of ionic bonds formed with a metal cation depends on the valency of the metal cation.

The metal cation may be selected from monovalent, divalent, or higher valent cations that are used in medicine (both therapeutic and diagnostic of human and animal subjects), in the cosmetics field or in agriculture. Thus, the metal cation must be pharmaceutically acceptable when used for medicinal applications, must be cosmetically acceptable when used in cosmetic applications or must be agriculturally acceptable when used in agricultural applications. Generally, “pharmaceutically acceptable” means suitable for administration to humans and animals (particularly mammals) with no substantial, major, or lethal adverse events. “Cosmetically acceptable” means considered non-toxic and safe to humans and animals (particularly mammals) at levels employed on skin areas and “agriculturally acceptable” suggests that the material is substantially not damaging or toxic to a plant or its environment, and not unsafe to the user or others who may be exposed to it, directly or indirectly, through accidental (passive) exposure or contact or consumption.

The cations may be selected amongst alkali metals, alkaline metals, and transition metals. Non-limiting examples include lithium, sodium, potassium, calcium, magnesium, manganese, aluminum, zinc, nickel, iron, silver, gold, barium and others.

In some embodiments, the metal is selected from sodium, potassium and calcium.

In some other embodiments, the material comprises a phosphonium cation and a phenolate compound.

The ammonium salt form is one which comprises the ammonium cation and a phenolate compound. The ammonium cation may be selected from any ammonium cations having a central positively charged nitrogen atom. In other words, the ammonium may be of the form $NH_4^+$, $NH_3R^+$, $NH_2RR'^+$, $NHRR'R''^+$ or $NRR'R''R'''^+$, wherein each of R, R', R'' and R''' may be a functionality that is covalently linked to the nitrogen atom, e.g., an alkyl group or an aryl group. For example, where the material comprises a single phenol-containing active material, namely a single phenolate group, the cation may be $NH_4^+$, or may be any of $NH_3R^+$, $NH_2RR'^+$, $NHRR'R''^+$ and $NRR'R''R'''^+$, wherein each of the R groups may be same or different and independently selected from alkyls and aryls.

Wherein one or more (or each) of the R groups above is an "alkyl", it typically contains between 1 to 20 carbon atoms, provided that the material remains water-soluble. Thus, in some embodiments, the alkyl comprises between 1 and 6 carbon atoms, in a straight or branched form. Exemplary alkyl groups include, without limitation, methyl, ethyl, propyl, isopropyl, isobutyl, n-butyl, sec-butyl, tert-butyl, isohexyl, and others.

The alkyl group also encompasses a "cycloalkyl" group, namely a saturated mono- or multi-cyclic ring system, in certain embodiments of 3 to 10 carbon atoms, in other embodiments of 3 to 6 carbon atoms. The ring system of the cycloalkyl may be composed of one ring or two or more rings which may be joined together in a fused, bridged or sprio fashion.

As "aryl" group is an aromatic monocyclic or multicyclic group containing from 6 to 20 carbon atoms. Aryl groups include, but are not limited to, unsubstituted or substituted fluorenyl, unsubstituted or substituted phenyl, and unsubstituted or substituted naphthyl.

The aryl group also encompasses a "heteroaryl" group which comprises a monocyclic or multicyclic aromatic ring system, in certain embodiments, of from 3 to 15 atoms, where one or more, in some embodiment-1 to 3 of the atoms in the ring system is a heteroatom selected from nitrogen, oxygen, sulfur and other non-carbon atoms. The heteroaryl group may be optionally fused to a phenyl ring.

In some embodiments, the ammonium cation may be $NH_4^+$ or a tetra-alkyl ammonium cation. Non-limiting examples of tetra-alkyl ammonium cations include tetramethylammonium, tetraethylammonium, tetrabutylammonium, tetrapentylammonium and tetrahexylammonium, or mixed alkyl forms. Another example is choline, or a choline derivative, or a poly choline such as di-choline or tri-choline as known in the art.

In some embodiments, the ammonium cation may be part of a polyamine having a multiple number of amine groups (including for example primary, secondary, and tertiary amines), which can be converted into a material as described herein by associating therewith a plurality of active phenol materials.

Where the material comprises two or more phenolate groups (on a single phenol-containing material), each of the phenolate groups may be ionically associated with a different cation, e.g., one may be associated with an ammonium cation while another may be associated with a metal cation, or each of the phenolates may be associated with a different or same metal cation.

The material comprising the phenolate entity is any phenol-containing active material (which may be a pharmaceutical ingredient, a cosmetic ingredient or an agricultural ingredient) used in medicine, cosmetics, veterinary or agriculture that has been transformed into the phenolate form by abstracting a hydrogen atom from the phenol —OH group. As stated herein, the phenolate compound may comprise one or two or more —OH groups on an aromatic carbocyclic group (a benzene or phenyl ring).

A material in the form of a metal complex may comprise one metal in a charged form (cation) that is ionically associated with one or more phenolate groups, wherein the number of phenolate groups is determined by the valency of the metal ion. For example, where an alkali metal atom such as lithium is used, the material may comprise the lithium ion and a single phenolate compound. The single phenolate compound may be a compound having one or more —OH groups; however, association between the metal ion and the phenolate compound may be via a single phenolate group.

Similarly, a metal complex may comprise a bivalent metal ion and two phenolate compounds, the two may be the same or different, i.e., the —OH which substitutes a benzene ring may be on the same benzene ring or on different benzene rings, or alternatively the two phenolate compounds are two separate phenol-containing compounds which may be same or different molecules. Putting it differently, metal ions, ammonium ions, or phosphonium ions which form an ionic bond with phenolate compounds may be provided as one or more of the following:

(1) —OH groups substituting a single benzene ring forming an ionic bond with one metal ion, ammonium ion, or phosphonium ion.

(2) —OH groups substituting different benzene rings, but on the same molecule (such as a polyphenolic or heterocyclic compounds), forming ionic bonds with one or more metal ions, ammonium ions, or phosphonium ions.

(3) —OH groups substituting same or different benzene rings on two distinct molecules (that are same or different) forming ionic bonds with one or more metal ions, ammonium ions, or phosphonium ions.

(4) any combination of the above.

The ionic bonding between the metal ion and the phenolate group may be with one metal ion or a plurality of metal ions, depending on the valency thereof as described herein. For example, a divalent ion may form one or two ionic bonds in any of the above (1) to (4) forms.

Scheme 1 below presents a general depiction of some of the metal complexes of the invention, wherein R= designates a substituent on a phenol-containing active material, the substituent may be an alkyl, aryl, or a heterocyclic group as defined hereinabove, or a ring fused to the phenol; and M is a mono, di and trivalent metal ion or an ammonium cation:

Scheme 1

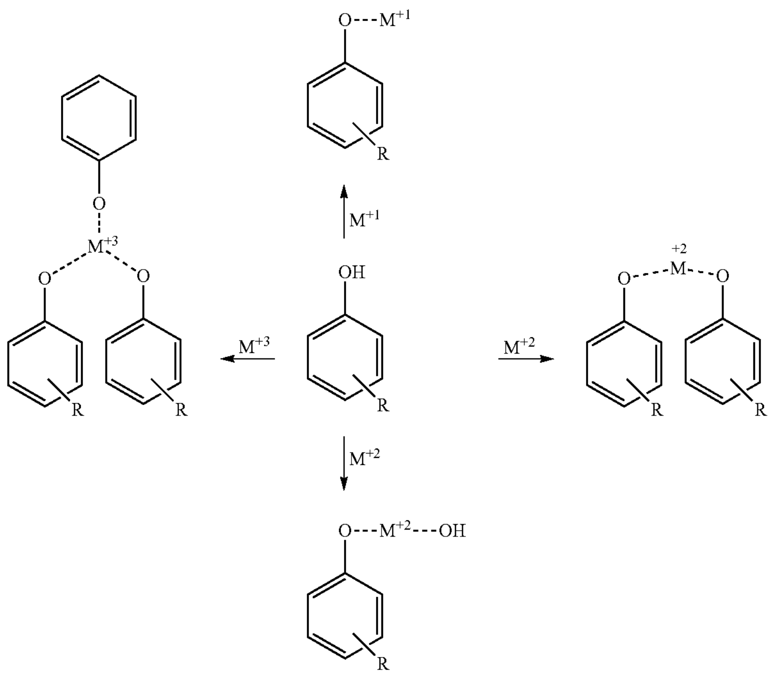

In Scheme 1 above, four different exemplary embodiments of the invention are depicted. In each case, the phenol is generally depicted, wherein R is a substituent group, a ring fused to the phenol or any derivation of the phenol-containing material.

The depicted phenol may comprise a single phenolic —OH group or more than one phenolic —OH group. In other words, each of the indicated phenol may comprise one, two or more hydroxyl groups that are directly associated with an aromatic carbocycle.

In the first case depicted in Scheme 1, the phenol-containing material is reacted with a monovalent metal $M^{+1}$ (in the form of a base that may be an alkali metal hydride, an alkali metal alkoxide, etc., generally in the form of M-X, wherein M is the metal cation and X represents the anion) or with ammonia (or an equivalent thereof), to form a complex between the phenolate compound (the anion of the phenol formed upon interaction with the base) and the metal cation or the ammonium cation, respectively.

In the second and third cases depicted in Scheme 1, the phenol-containing material is reacted with a divalent metal $M^{+2}$ (in the form of a base that may be an alkaline earth metal hydride, an alkaline earth metal alkoxide, etc., generally in the form of M-X, wherein M is the divalent metal cation and X represents the dianion), to form a metal salt with two phenolate groups or between a single phenolate group and another anion (not a phenolate). The two phenolate groups may be the same or different.

In the fourth case depicted in Scheme 1, the phenol-containing material is reacted with a trivalent metal $M^{+3}$ (in the form of a base that may be a trivalent metal trihydride, a trivalent metal trialkoxide, etc., generally in the form of M-X, wherein M is the trivalent metal cation and X represents the trianion), to form a metal complex between three phenolate groups and the trivalent metal cation. In some embodiments, the three phenolate compounds are the same, and in other cases they are different. In some embodiments, two of the three are the same and the third is different. In some embodiments, each of the three is different from the other, all with respect to the described above. The counterion of the phenolate can be prepared by exchanging a counterion by displacement in solution, for example, phenolate sodium salt may be converted into the calcium or choline salt by immersing in a solution of calcium salt of choline salt so that the sodium counterion is replaced by the ion in solution.

In case of a catechol molecule where two phenolic —OH groups are ortho on the same aromatic ring or otherwise close to each other, they may form an ionic complex with one divalent or trivalent metal ion such as calcium, magnesium or iron as depicted in Scheme 2 below, where R and M are as defined for Scheme 1:

Scheme 2

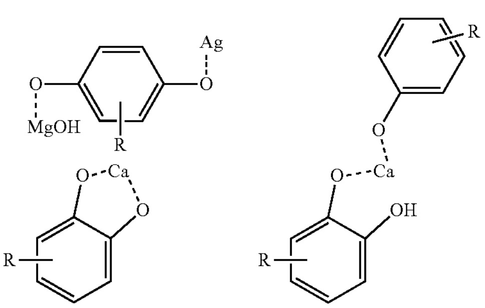

-continued

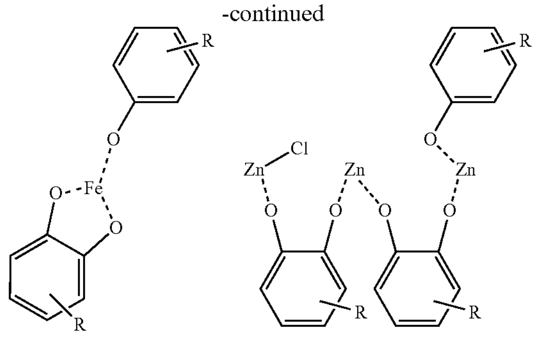

In case of a divalent or trivalent metal ion such as iron or alumina, a mix interaction with other functional groups may be formed. For example, calcium ion may bind to a phenolate anion and to a carboxylate anion (as shown in Scheme 3 below) or in the case of iron, one or two phenolate anions bind to trivalent iron ion and the third valent may form a coordination adduct.

Scheme 3

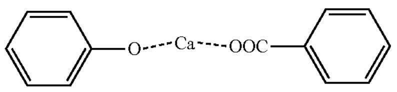

In a material of the invention, where two or more phenolate groups are associated to a metal cation, each of the phenolate groups may be of an active material, at least one of the phenolate groups may be of an active drug material, only one of the phenolate groups is of an active material, or the majority of the phenolate groups are of active materials. In some embodiments, where two or more phenolate compounds are associated to a metal cation, one of the phenolate compounds is an active material and another of the phenolate compounds is a different active material or a non-active drug material.

As used herein, an active material is any therapeutic, cosmetic or veterinary material that is typically used, respectively, in methods of treatment or prophylaxis of a disorder or disease state, or in methods to improve the state or condition of a skin region (or generally in cosmetic methods of use), or any condition related to the human or animal body, or in methods of treatment or facilitation of plant diseases and disorders or generally in plant protection or other agricultural methods.

A phenol-containing compound that is used in agriculture is any such compound that is used as an herbicide, a fungicide, an insecticide, a rodenticide, a plant growth regulator, a hormone, an attractant, a repellent, a nutrient, a fertilizer and others.

The phenolate compound or the phenol-containing bioactive is not phenol ($C_6H_6OH$), or any substituted form thereof.

In some embodiments, the phenol-containing bioactive is an active material comprising one phenolic —OH group and at least one other functional group. In some embodiments, the active material is a material comprising two or more phenolic —OH groups and at least one other functional group. In some embodiments, the active material is a material comprising multiple phenolic —OH groups and optionally at least one other functional group. In some cases, the aromatic ring bearing an —OH group may include one, at times 2, at times 3 and at times 4, at times 5 and at times 6 —OH group.

The "at least one other functional group" is a group different from —OH, which may be any functional group substituting a position on the aromatic ring that is not a hydroxyl group (—OH) and not a hydrogen atom (—H). The functional group may be selected from a halide atom, haloalkyl, nitro, alkoxy, alkylthio, aryloxy, arylthio, haloalkoxy, carboxylic acid, ester, ether, amide, alkylaminocarbonyl, carboxamide, arylalkylaminocarbonyl, arylaminocarbonyl, arloxycarbonyl, alkyl, alkenyl, alkynyl, azaalkylene, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene, heterocyclylene, sulfinyl, sulfo, amine and others.

In some embodiments, the phenol-containing active material comprises a fused aromatic group, i.e., a benzene or phenyl ring that is directly substituted with a hydroxyl group. The fused ring system may be in the form of a phenol group fused to a cyclic carbocycle or heterocycle (containing also one or more heteroatoms such as N, S, O) which may be aromatic or non-aromatic. Such systems are generally referred to as heterocyclic systems.

In some embodiments, the phenol-containing active material comprises a single phenol group such as simple phenols (however, excluding phenol and simple derivatives thereof) and benzoquinones. Non-limiting examples of such compounds include catechol, hydroxyquinone and 2,6-dimethoxybenzoquinone.

In some embodiments, the phenol-containing active material is a phenolic acid or a phenolic aldehyde such as gallic acid and salicylic acid.

In some embodiments, the phenol-containing active material is selected amongst acetophenones, tyrosine derivatives and phenylacetic acids. Non-limiting examples include 3-acetyl-6-methoxybenzaldehyde, tyrosol and p-hydroxyphenylacetic acid.

In some embodiments, the phenol-containing active materials selected amongst hydroxycinnamic acids, phenylpropenes and coumarins. Non-limiting examples include caffeic acid, ferulic acid, myristicin, eugenol, umbelliferone, aesculetin, bergenon and eugenin.

In some embodiments, the phenol-containing active material is selected amongst naphtoquinones. Non-limiting examples include juglone and plumbagin.

In some embodiments, the phenol-containing active material is selected from xanthonoids such as mangiferin.

In some embodiments, the phenol-containing active material is selected from stilbenoids and anthraquinones. Non-limiting examples include resveratrol and emodin.

In some embodiments, the phenol-containing active material is selected from chalconoids, flavonoids, isoflavonoids and neoflavonoids. Non-limiting examples include quercetin, cyaniding and genistein.

In some embodiments, the phenol-containing active material is selected from lignans and neolignans. Non-limiting examples include pinoresinol and eusiderin.

In some embodiments, the phenol-containing active material is selected from bioflavonoids. Non-limiting examples include amentoflavone.

In some embodiments, the phenol-containing active material is selected from lignins, catechol melanins, flavolans (such as condensed tannins), polyphenolic proteins and polyphenols. Non-limiting examples include raspberry ellagitannin and tannic acid.

In some embodiments, the phenol-containing active material is a hormone selected from estradiol, thyroxine, levothyroxine, triiodothyronine, adrenaline, and others.

Additional non-limiting examples of such phenol-containing active materials include cannabinoids, fenoldopam, tyrosine, xylenol, thymol, propofol, apomorphine, morphine and derivatives thereof, mitoxantrone, dexorubicine, hexachlorophene, acetaminophen, p-coumaric acid, 3,4-dihydroxybenzoic acid, 4-hydroxybenzoic acid, butylparaben, vanillic acid, guaiacol, caffeic acid, tolterodine, raloxifea, scopoletin, decursinol, dopamine, L-DOPA, curcumin, polyphenols, tianine and others.

In some embodiments, the phenol-containing active material is salcaprozate sodium (SNAC).

In some embodiments, the phenol-containing active material is tapinarof.

In some embodiments, the phenol-containing active material is of a cinnamon extract.

In some embodiments, the phenol-containing active material is any one or more of mesalazine, salbutamol, pirbuterol, capsaicin, salmeterol, vilanterol, balsalazide, labetalol, mycophenolic acid, pyridoxine, phenylephrine, edrophonium, paracetamol, monobenzone, tapentadol, metaraminol, metirosine, oxymetazoline, nabilone, diflunisal, olsalazine, liothyronine sodium, desvenlafaxine, rotigotine, phentolamine, oxyphenbutazone, amodiaquine, olodaterol, troglitazone, eltrombopag, ivacaftor, indacaterol, cefadroxil, cefprozil, tetrahydrocannabinol, estradiol, estradiol valerate, estradiol cypionate, levallorphan, oxymorphone, nalbuphine, buprenorphine, butorphanol, naloxone, levorphanol, naltrexone, dezocine, morphine, naloxegol, methylnaltrexone, nalmefene, metacycline, sarecycline, omadacycline, eravacycline, equilin, flutemetamol, diethylstilbestrol, dienestrol, probucol, mitoxantrone, bazedoxifene, raloxifene, arbutamine, dobutamine, masoprocol, cannabidiol, terbutaline, orciprenaline, denoldopam, norepinephrine, corbadrine, isoprenaline, isoetarine, droxidopa, carbidopa, protokylol, apomorphine, entacapone, tolcapone, idarubicin, daunorubicin, doxorubicin, epirubicin and valrubicin.

In some embodiments, the phenol-containing active material is a cannabinoid material. The cannabinoid material may be selected amongst tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), and others.

In some embodiments, the cannabinoid is THC or CBD.

In some embodiments, the material comprises a phenolate form of at least one cannabinoid and one or more metal cation selected from sodium, potassium and calcium.

Metal complexes with the phenol-containing active material, e.g., CBD, improves chemical stability by preventing oxidation or thiol substitution due to removal of electron density from the aromatic ring; improves water solubility due to presence of the ionic nature, which can be easily reversible with the addition of dilute acid to reform the phenols.

The cannabinoid material may be a synthetic or natural cannabinoid(s), a *cannabis* extract(s) or a fraction thereof. In the broadest sense, this term refers to the entire class of chemical compounds, cannabinoid/cannabinoid agonists/cannabinoid-related compounds, acting with various affinities on the endogenous cannabinoid receptors (CB1 and CB2). This group of ligands include the endocannabinoids (produced naturally by humans and animals), Phyto cannabinoids (found in *cannabis* and some other plants), and synthetic cannabinoids (manufactured artificially). Such term further refers to the classical cannabinoids originating from or mimicking the natural cannabinoids in a *cannabis* plant.

In some embodiments, the cannabinoid material (comprising a phenolic group) may be selected from any one of the above materials.

Another advantage of *cannabis*-based compositions is in their added content of terpenes, sesquiterpenes, carotenes, flavonoids, being present in various combinations and proportions, and which contribute to absorption, activity and further to flavor-, odor-, and color-imparting properties, in the sense of being more user-friendly. Thus, a phenol-containing active material may be any of terpenes, sesquiterpenes, carotenes, flavonoids which are present in a *cannabis* plant and contains a phenolic group therein.

A variety of phenolic salts of drug entities have been prepared by simple chemical reactions at ambient conditions. Scheme 1 depicts general approaches for their preparation. Amongst the complexes formed is a cannabinoid such as CBD, as shown in Schemes 4, 5 and 6 below.

As depicted in Scheme 4 below, CBD metal complexes are easily prepared from the reaction of CBD with the corresponding metal hydroxides or chloride salts under basic conditions. CBD complex is converted back to the phenol form by addition of dilute HCl. Each M is as defined above for Scheme 1.

Scheme 4

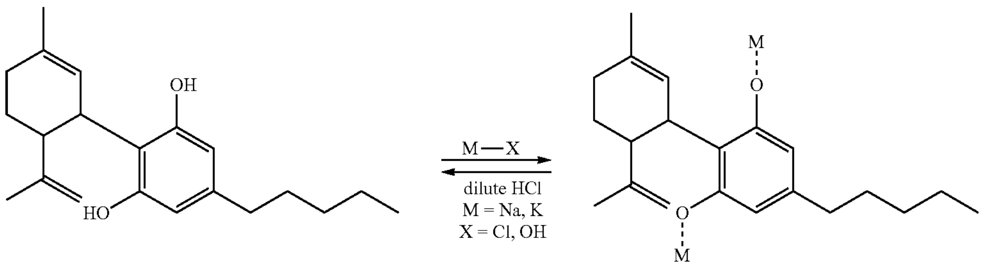

Metal complexes of the invention displayed dramatic water solubility (10 mg/mL, nearly 800× more soluble than CBD), as summarized in Table 1 below.

Multivalent metal centers may be used to form salts with multiple CBD molecules (Scheme 5). Metal salts via the phenols of CBD may further enhance chemical stability and physical properties of CBD. Scheme 5 shows CBD dimer or trimer metal salts and depicts their simple synthesis from the reaction of CBD with correspondent divalent metal sulfate or chloride salts under basic conditions. The CBD salt was converted back to the phenol form by addition of dilute HCl. Each M is as defined for Scheme 1.

CBD was also reacted along with other phenolic biologically active compounds such as L-Dopa, Dopamine, and Curcumin (Scheme 6). The CBD heterodimer metal salts were synthesized from the reaction of CBD and other phenolic compounds (L-Dopa, dopamine, curcumin) with the correspondent divalent metal sulfate or chloride salts under basic conditions.

Scheme 5

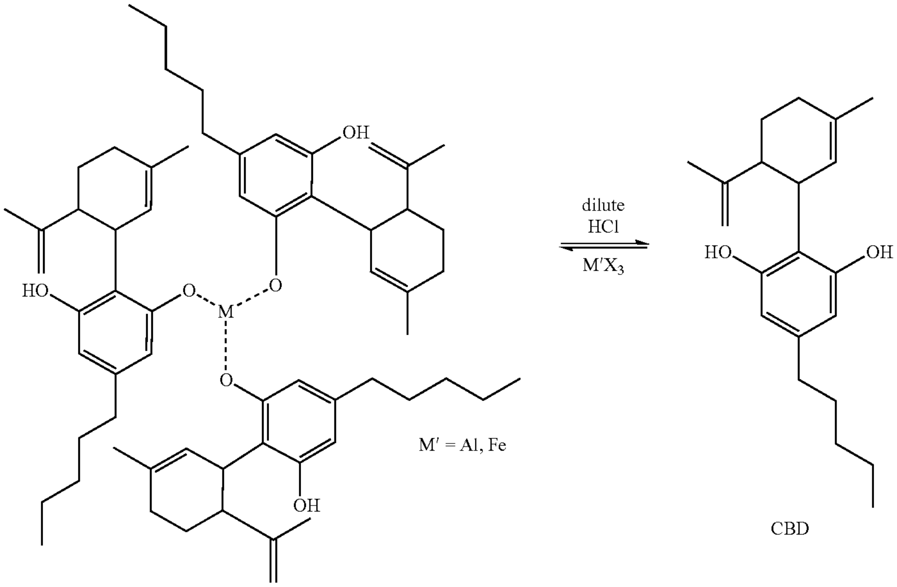

CBD homotrimer

CBD

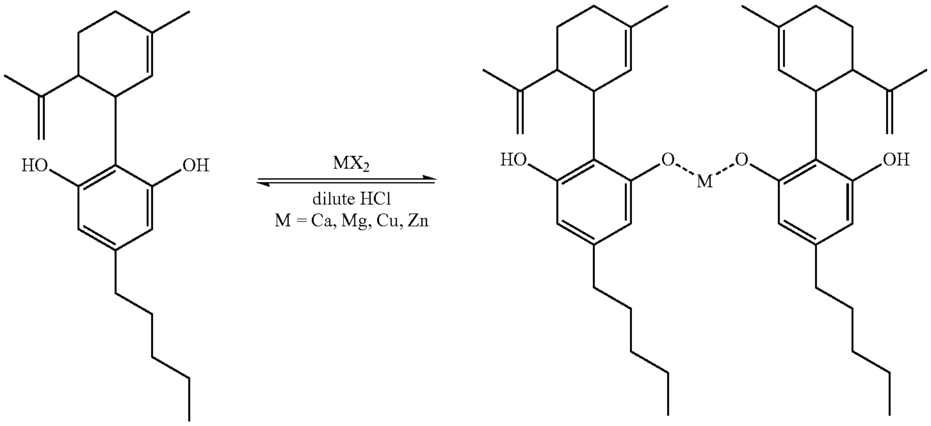

CBD

CBD homodimer

Scheme 6

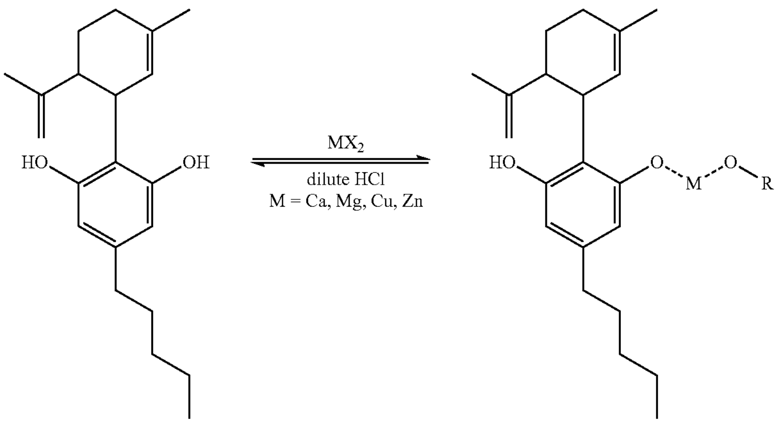

CBD

CBD heterodimer

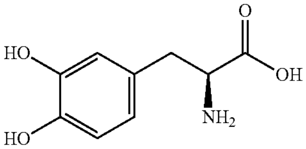

L-Dopa

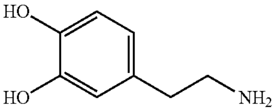

Dopamine

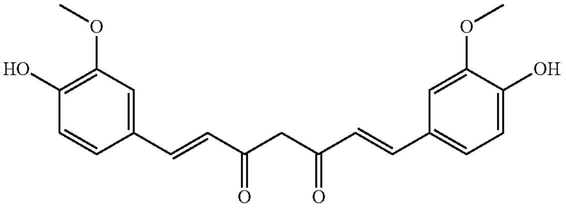

Curcumin

R = dopamine, L-Dopa, Curcumin

The invention further provides a CBD salt with sodium or calcium. The metal complexes are thus sodium-CBD and calcium di-CBD.

The invention further provides metal salts of at least one metal cation, as defined, and at least one cannabinoid, wherein the at least one cannabinoid is an isolated cannabinoid or present in a composition, e.g., a *cannabis* plant extract, with at least one other cannabinoid that is not in the form of a metal complex of the invention. Such mixed forms may be formed by reacting a *cannabis* extract under basic conditions with a metal cation to cause phenolate ions to form and associate with the metal cation. As not all naturally occurring cannabinoids or naturally occurring plant components present in a cannabinoid extract contain phenol groups, selective association between the phenol bioactives and the metal cation should occur. In some cases, the ionic bond may be formed between a cannabinoid such as CBD and another material contained in a *cannabis* plant such as terpene, sesquiterpene, carotene or a flavonoid.

Generally speaking, phenol-containing active materials of the invention are provided in isolated forms, in extract forms, in purified forms and as drug actives in formulations for medicinal, cosmetic, veterinary or agricultural use. Where the actives are isolated, they may be in a substantially pure form, namely in purity of between 95 and 100%.

The invention further provides pharmaceutical, cosmetic, agriculture, food or veterinary formulations or compositions comprising at least one material according to the invention.

In numerous embodiments, compositions of the invention can further comprise antioxidants, absorption enhancers, color- and flavor-imparting agents, preservatives, stabilizers, salts, in various combinations. Various sweeteners, taste modifiers, antioxidants, preservatives which are well known in the art include taste modifiers such as artificial sweeteners, flavorings as strawberry and peppermint oil, for example, plant sweeteners, sugars, honey, *Stevia*, steviol, glycosides, citrate, acids, menthol, anise, *eucalyptus* oil, fennel, natural antimicrobial substances and natural antioxidant (e.g. extracts of murta, oregano, rosemary, borage), antioxidants such as vitamins E (tocopherol) and C and their derivatives, butylated hydroxy anisole (BHA), butylated hydroxytolune (BHT) recognized as GRAS, and sulfides; any sweetener allowed for oral administration such as sugar, glucose, sucralose, glycine, cyclamate, sucrose, saccharin, fructose, maltose, *stevia* extract, sodium saccharine; salts such as NaCl, citrate, and others.

It should be noted that compositions of the invention are adaptable for any type of administration, as known in the medicinal or veterinary sciences. Formulations of the invention may be configured or engineered or adapted or selected or used for topical administration (e.g., in a form of a cream and an ointment), enteral administration (e.g., including all systemic administration routes involving administration via the gastrointestinal tract, such as oral administration), or parenteral administration (e.g., including all systemic administration routes, not involving administration via the gastrointestinal tract). Non-limiting administration routes effective for administration of formulations of the invention include oral, sublingual, mucosal, aerosol, inhalation, parenteral, subcutaneous, intravenous, intramuscular, intraperitoneal, rectal and vaginal administrations.

As has been mentioned, it is another aspect of the invention to provide dosage forms for oral or sublingual administrations comprising the previously described formulations.

Additionally, the material of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate for such uses.

In numerous embodiments, the oral dosage forms of the invention can comprise at least one synthetic or natural cannabinoid metal or ammonium salt which is THC, CBD, CBN, CBG, CBC, CBL, CBV, THCV, CBDV, CBCV, CBGV, CBGM, as a derivative, or a precursor.

In yet other embodiments, oral dosage forms of the invention can comprise a *cannabis* extract or a fraction obtained from a strain *C. Sativa, C. Indica, C. Ruderalis* or a combination thereof, wherein some of the materials therein are in their phenolic metal salt form.

As noted above, the oral dosage forms of the invention can further comprise additional therapeutic agents, minerals, nutrients, vitamins in various concentrations and combinations.

Of particular interest are oral dosage forms with a controlled release property. The term "controlled release" refers to a property or a modification enabling to achieve time dependent release, sustained release, prolonged release and also pulse release, i.e., delayed release of the drug. The term further relates to gastro-resistance, i.e., a property or a modification enabling to achieve pH-controlled drug release, gastrointestinal targeting, colon delivery, protection of acid-sensitive actives, protection of gastric mucosa from aggressive actives. In this sense, gastro-resistance is also targeted drug release. Gastro-resistant coatings and modifications are also known to improve storage stability.

Improved gastro-resistance and/or controlled release can be achieved by modification of and/or coating using various pharmacological technologies, such as use of poly(meth) acrylates or layering. A well know example of poly(meth) acrylate coating which has been widely used in the pharmaceutical industry to achieve targeted and controlled drug release is EUDRAGIT®. Another important feature of poly (meth)acrylate coating is protection from external influences (moisture) or taste/odor masking to increase patient compliance.

Certain solid oils can be added to facilitate controlled release, such as mono-, di- and triglyceride oils, in general, and trilaurin, tricaprin, tripalmitin, trimyristin, glyceryl, hydrogenated palm oil distearate, hydrogenated castor oil, hydrogenated vegetable oil, in particular.

In certain embodiments, oral dosage forms of the invention can comprise matrix modifying/controlled release materials, which include, although not limited to, glycerides, waxes, fatty acids, polymers of methyl acrylate or methyl methacrylate, ethyl cellulose, poly(vinyl alcohol) (PVA), poly(vinyl pyrrolidone) (PVP), starch, chitosan, and others.

In other embodiments, oral dosage forms of the invention can be coated with hydroxypropyl methylcellulose, polyacrylates, methyl acrylate-methacrylic acid copolymers, cellulose acetate, polyvinyl acetate phthalate, and other types of coatings.

In numerous embodiments, the oral dosage forms of the invention can be provided in the form of a tablet or a capsule, both being the most popular and convenient methods of oral drug delivery. The capsules may be provided with a coating that is a gastro-resistant coating using GRAS-based materials.

In further embodiments, the dosage forms can use a secondary package, such as a blister (PVC/PVDC—Alufoil), a bottle, an aluminum pouch and others.

In another aspect, the formulations and compositions of the invention can be applied for the treatment and alleviation of several diseases and medical conditions. Such medical conditions may be those which demonstrate a beneficial therapeutic effect when administering the composition. All compositions or formulations of the invention comprise at least one active material having a phenolic group and a metal, ammonium or phosphonium cation ionically bound thereto.

In yet another aspect, the above-described formulations, compositions and dosage forms of the invention can be applied for the treatment and alleviation of several diseases and medical conditions, specifically those wherein beneficial effects of cannabinoids or *cannabis*-based medicines have been previously demonstrated. In other words, the invention provides a range of therapeutic methods for treating diseases or medical conditions related to beneficial effects of cannabinoids or *cannabis*, by application of presently described formulations, compositions, or dosage forms. As to be noted, the therapeutic methods of the invention can be applied to a wide range of human conditions, including inflammatory, neurological, psychiatric disorders, malignancies and further immune, metabolic disorders, nutritional deficiencies, infectious diseases, and types of gastrointestinal disorders, cardiovascular disorders, and various types of pain, including chronic and neuropathic pain.

Considering the present level of knowledge regarding clinical applications of cannabinoids in young and elderly patients, it is projected that the presently described preparations and methods can be applied to, although not limited to depression, sleeping disorders, eating disorders, cancer, multiple sclerosis, graft versus host disease (GVHD), Parkinson's, epilepsy, autism, tuberculosis, ulcerative colitis, morbus Crohn, inflammatory bowel disorder (IBD), irritable bowel syndrome (IBS), appetite stimulant, appetite depressant, obesity, nausea, neuropathic pain, anxiety, Alzheimer's disease, amyotrophic lateral sclerosis (ALS), gastrointestinal disorders, hypertension, incontinence, pruritus, arthritis, arthrosis, rheumatic inflammation, insomnia, mycosis, local and/or chronic pain, inflammation, attention deficit and hyperactivity disorder (ADDH), vomiting, atopic dermatitis, fibromyalgia, AIDS, mood disorders, erectile dysfunction, premature ejaculation, nutritional deficiency.

It should be appreciated that the presently described preparations and methods are applicable to subjects that are infants, adolescents, or adults.

It should also be noted that formulations, compositions, and dosage forms of the invention are applied in therapeutically effective amounts. In general terms, a "therapeutically effective amount" (also a pharmacologically or a pharmaceutically or a physiologically effective amount) denotes an amount of the material of the invention needed to achieve the anticipated or desired physiological response. The precise amount is dependent on numerous factors, e.g., the type of agent, activity and intended use (e.g. number of doses per day), which can be determined by technologies and methods known in the art. It is understood that the effective amount can be the result of empirical and/or individualized (case-by-case) determination on the part of the treating health care professional and/or individual. The administration of larger therapeutic doses can involve multiple daily administrations.

The terms "treating", "treatment" or "therapy" or any lingual variation thereof, refer equally to curative therapy, ameliorating therapy or prevention therapy. The terms encompass any approach for obtaining beneficial or desired therapeutic effects, which may be established clinically by means of physiological, metabolic, or biochemical parameters. Beneficial or desired clinical results include, but are not limited to, alleviation of symptoms, diminishment of extent of disease, stabilization of symptoms, delay or slowing of progression, amelioration or palliation of a condition or a symptom, and remission (whether partial or total). The term "palliation" encompasses herein undesirable manifestations of a physiological condition or a symptom which are lessened and/or a progression which is slowed or lengthened, as compared to the same but untreated condition. The terms may also relate to the prevention of a disease or a disorder.

Still further, in certain embodiments, preparations and methods of the invention involve combination therapies, administered simultaneously or in succession with other methods and drugs (also therapeutic agents).

Therapeutic agents that are relevant can be, although not limited to, General Drug Categories, classified by the FDA according to their clinical effects and applicability to common human disorders: analgesics, antacids, antianxiety drugs, antiarrhythmics, antibacterials, antibiotics, antimicotics, anticoagulants and thrombolytics, anticonvulsants, antidepressants, antidiarrheals, antiemetics, antifungals, antihistamines, antihypertensives, anti-inflammatories, antineoplastics, antipsychotics, antipyretics, antivirals, barbiturates, beta-blockers, bronchodilators, cold cures, cholesterol lowering drugs, corticosteroids, cough suppressants, cytotoxics, decongestants, diuretics, expectorant, hormones, hypoglycaemics, immune-suppressive, laxatives, muscle relaxants, sedatives, sex hormones, sleeping drugs, tranquilizer and vitamin supplements.

In terms of therapeutic effects, an improvement as a result of treatment is identified if there is at least about 5% improvement, or 10% improvement, or at least 25%, or at least 50%, or at least 75%, or at least 100% improvement or more. An improvement herein can be interpreted in the sense of individual improvement as well as population improvement.

The term "about" in all its appearances in the text denotes up to a ±10% deviation from the specified values and/or ranges, more specifically, up to 1%, ±2%, 3%, 4%, 5%, 6%, 7%, 8%, 9% or ±10% deviation therefrom.

The invention further provides use of at least one metal or ammonium salt of the invention in the preparation of a formulation, or in a method of prophylaxis or treatment of at least one disorder or disease state as described herein.

Also provided is a use of at least one metal or ammonium salt as described herein for treating a disease or a disorder which found to be treatable by utilizing a phenol containing material (e.g., CBD).

Also provided is a use of at least one material as described herein for the preparation of a formulation, a pharmaceutical composition or a medicament as described herein for treating, preventing or ameliorating a disease or a disorder which is found to be treatable by such composition of materials.

Also provided is a use of the composition or formulation of the invention for protecting and treating plants and crops from bacterial and/or fungal infections.

In some embodiments, the material comprised in the formulation is selected from sodium chlorite, copper salicylate, bromochlorodimethylhydantoin, copper thymol, and polyguanidine. However, many other phenol-containing active materials may be employed for producing a material which is appropriate for treating plants and crops.

In some embodiments, the bacteria/fungal infections are selected from *erwinia, pythium, Macrophomina phaseolina, athelia rolfsii* and potato scab. However, any other infection related to a plant or a crop that may be treatable by utilizing the materials of the invention is also an embodiment of the herein invention.

Further provided herein is a composition or a formulation comprising a material, wherein the material comprising a polyvalent metal cation having a valency of at least ($^{2+}$) and at least one active material comprising at least one phenolate moiety ionically bonded to the polyvalent metal cation, wherein the composition or the formulation is for use in treating a disease or disorder which is treatable by administering to a subject a therapeutically effective amount of the composition or the formulation.

Also provided is a composition or a formulation comprising a material, wherein the material comprising an ammonium cation as defined herein or a poly-ammonium, and at least one active material comprising at least one phenolate moiety ionically bonded to the ammonium or the poly-ammonium cation, wherein the composition or the formulation is for use in treating a disease or disorder which is treatable by administering to a subject a therapeutically effective amount of the composition or the formulation.

Still further, there is provided a method for treating a disease or disorder which is treatable by administering to a subject a therapeutically effective amount of a composition or a formulation comprising a material, wherein the material comprising an ammonium cation as defined herein or a poly-ammonium or a polyvalent metal cation having a valency of at least ($^{2+}$), and at least one active material comprising at least one phenolate moiety ionically bonded to the ammonium cation or the poly-ammonium or the polyvalent metal cation.

The invention further provides a method of preparing a material according to the invention, the method comprising treating at least one phenol-containing active material with a base, e.g., comprising a metal cation or ammonia or an equivalent thereof, as defined herein. The base may be selected from a metal hydride, a metal alkoxide, an alkali metal hydroxide, an alkaline earth metal hydroxide, metal carbonates, metal carbanions, metal amides, ammonia (as described herein, e.g., choline) and others.

As described herein, another way to alter and improve the physico-chemical properties of a phenol-containing active material is by forming ammonium salts thereof, to thereby produce a salt comprising a phenol-containing material and an optionally substituted ammonium cation. Therefore, in another one of its aspects, the invention provides an ammonium salt of at least one phenolic (or phenol containing) material and at least one optionally substituted ammonium ion, wherein the phenol-containing active material is not phenol ($C_6H_6O$), methylphenol, bromophenol, dibromophenol, tribromophenol, pentachlorophenol, bisphenol A, tetrabromobisphenol A, resorcinol, hydroquinone, hydroquinone and naphthol.

A non-limiting schematic example of the synthesis of an optionally substituted ammonium-CBD material is demonstrated in Scheme 7:

Scheme 7

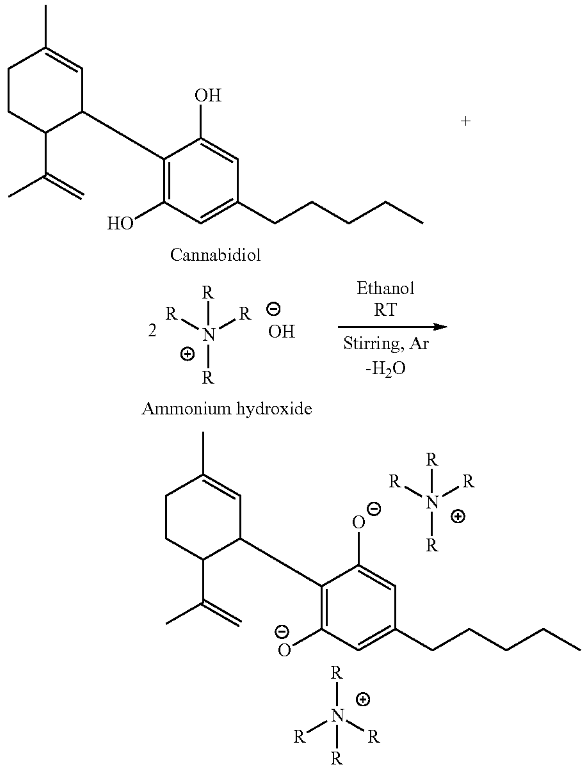

Cannabidiol

Ammonium hydroxide

Ammonium cannabidiol salt

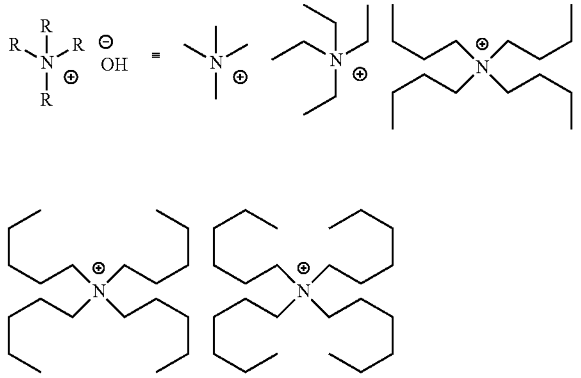

The reaction may be carried out in the presence of ammonia or an ammonium equivalent, as explained hereinabove. In Scheme 7, ammonium hydroxide is used. It may be selected amongst ammonium hydroxide (wherein each R is H), mono-alkylated ammonium hydroxide (wherein one of the R groups is alkyl and the others are each H), or multi (di, tri or tetra)-alkylated ammonium hydroxides.

In a similar fashion, other phenol-containing active materials used in various fields, such as medicine, cosmetics, veterinary and agriculture, as disclosed herein, may also be transformed into their ammonium phenolate forms.

The non-limiting example of fenoldopam is schematically demonstrated in Scheme 8:

Scheme 8

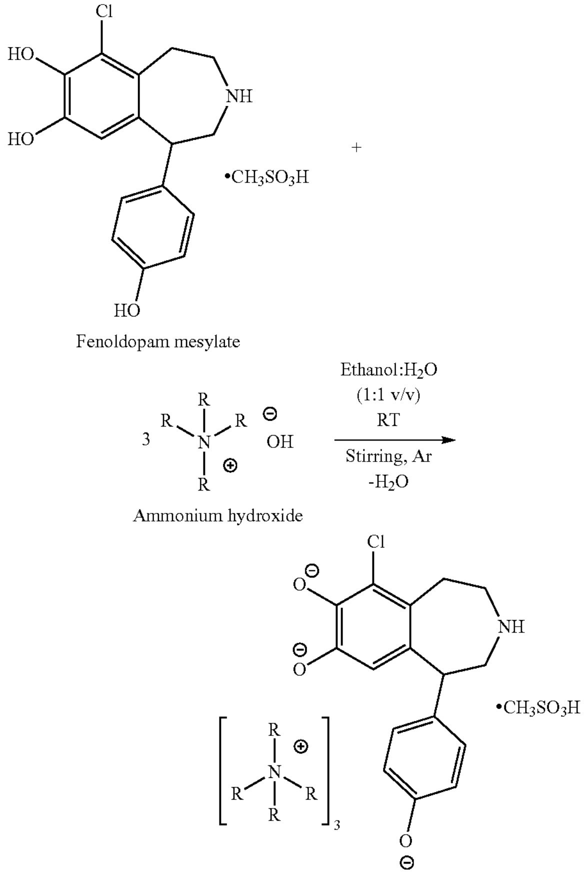

Fenoldopam mesylate

Ammonium hydroxide

Ammonium-Fenoldopam complex

Scheme 8 depicts synthesis of ammonium-fenoldopam complex using ammonium hydroxide. The reaction may be carried out in the presence of ammonia or an ammonium equivalent, as explained hereinabove. In this Scheme, ammonium hydroxide is used. It may be selected amongst ammonium hydroxide (wherein each R is H), mono-alkylated ammonium hydroxide (wherein one of the R groups is alkyl and the others are each H), or multi (di, tri or tetra)-alkylated ammonium hydroxides. Examples of such ammonium hydroxides are depicted in Scheme 7.

As a person versed in the art would know, the alkylated ammonium hydroxides may be constructed of simple alkyls or of highly substituted alkyls. The synthesis of such alkylated ammonium hydroxides is simple which may be used to react with phenol containing bioactive agent to form the corresponding ammonium salts. In a typical synthesis, trialkyl amine is reacted with alkyl halide in an organic solvent to form the tetra alkyl halide which then reacted with KOH to replace the halide with the OH moiety.

Any of the optionally substituted ammonium salts mentioned herein may also be obtained or synthesized by any other methods known in the literature, and the reagents which are used in the schemes may be exchanged to other suitable reagents known in the art.

Materials of the invention may be used as active ingredients in a variety of applications and fields (medicine, cosmetics, agriculture, chemical and biological industry, dyes, etc.). Where the counter ion is in the form of a polymer having one or a plurality of cationic centers, such as in the case of polyamines, such materials may also be used for preparing nano and microcapsules for delivery of other agents.

As used herein, the terms “nanoparticle”, “nanosphere”, “nanocapsule” and “particle” are all referring to a particulate carrier, which is biocompatible and sufficiently resistant to chemical and/or physical destruction, such that a sufficient amount of the nanoparticles remain substantially intact after administration into the human or animal body and for sufficient time to be able to reach the desired target tissue (organ). Generally, the nanoparticles are spherical in shape, having an average diameter of up to 1000 nm and in most of the times even up to 500 nm. Where the shape of the particle is not spherical, the diameter refers to the longest dimension of the particle.

When referring to “microcapsules”, the meaning is particles as described above having a diameter of between about 1 and 1,000 km.

The invention also provides a polycation associated with a plurality of phenolate active agents, and compositions comprising same.

The invention further provides a material according to the invention, being in the form of a multimolecular material comprising two or more phenol-containing active materials, each being ionically associated with a cation; wherein the cation is a multivalent metal cation or a poly-ammonium.

The terms “polyamines” and “poly-ammonium” generally refer to any compound having a plurality (usually at least three, but sometimes more than two) of amino functional groups. In some cases, such compounds are formed via decomposition of proteins. In some embodiments, such polyamines are alkyl polyamines. In some embodiments, the polyamines are natural polyamines and in other embodiments, the polyamines are synthetic.

In case the polyamines are natural, they may be selected without limitation from spermidine and spermine or any other triamines, tetraamines or polyamines which naturally appears in nature, and particularly in the human body.

In some embodiments, the polyamines are synthetic polyamines selected from diethylenetriamine, pentamethyldiethylenetriamine, triethylenetetramine, tetraethylenepentamine, pentaethylenehexamine, macrocyclic polyamines such as 1,4,7-triazacyclonane, cyclen and cyclam, branched polyamines such as tris(2-aminoethyl)amine and tripodal polyamines such as 1,1,1-tris(aminomethyl)ethane.

In some specific embodiments, the polyamine is dicholine or tri-choline.

In some embodiments, the polyamine is multi-choline polymer comprising at least three choline moieties. “Multicholine” according to the invention is a polymeric molecule having multiple (at least two) choline moieties.

In some embodiments, the multivalent metal cation is a divalent, a trivalent or a tetravalent cation, or a higher valent metal cation.

In some embodiments, the material is formed by a reaction of a polyphenol with the multivalent cation or polyammonium.

In some embodiments, the material is for use in the preparation of nanoparticles or microparticles. In some embodiments, the material is for use in the preparation of a coating material.

The invention also provides a particle comprising a material according to the invention.

Where the phenol-containing agent is not a pharmaceutically or otherwise an active agent, the invention provides a material in the form of a multimolecular material comprising two or more phenol-containing materials, each being ionically associated with a cation; wherein the cation is a multivalent metal cation or a poly-ammonium. In some embodiments, the multivalent metal cation is a divalent, a trivalent or a tetravalent cation or a higher valent metal cation.

In some embodiments, the material is formed by a reaction of a polyphenol with the multivalent cation or polyammonium.

In some embodiments, the material is for use in the preparation of nanoparticles or microparticles, or for use in the preparation of a coating material.

Thus, specific aspects and embodiments of the invention include: An isolated material comprising at least one phenol-containing active material and a metal salt, a phosphonium or an ammonium salt counter-ion, wherein the active material is not phenol (C6H6O), methylphenol, bromophenol, dibromophenol, tribromophenol, pentachlorophenol, bisphenol A, tetrabromobisphenol A, resorcinol, hydroquinone, hydroquinone or naphthol.

The material comprises a metal cation and a phenolate active material, wherein the bond associating the metal cation and a charged oxygen atom on the phenolate material is an ionic bond.

The material wherein the metal cation is selected from monovalent, divalent, and polyvalent cations.

The material wherein the metal cation is a divalent or trivalent metal cation.

The material wherein the metal cation is not a monovalent cation.

The material wherein the metal cation is selected amongst alkali metals, alkaline metals and transition metals.

The material wherein the metal cation is not an alkali metal.

The material wherein the metal cation is selected from lithium, sodium, potassium, calcium, magnesium, manganese, aluminum, zinc, nickel, iron, silver, gold barium metal cations.

The material when in the form of an ammonium salt.

The material when in the form of a phosphonium salt.

The material wherein the phenolic active material is a phenol-containing active material used in medicine, cosmetics, veterinary or agriculture, that has been transformed into the phenolate form by abstracting a hydrogen atom from the phenol —OH group.

The material wherein phenol-containing active material comprises one or more —OH groups.

The material when comprising a divalent metal and two phenolate active materials.

The material when comprising two or more phenolic-active materials, each active material having one or more phenolate groups, each of the phenolate groups being associated with a different cation selected from a metal cation, a phosphonium cation and an ammonium cation.

The material wherein the two phenolate active materials are the same or different.

The material comprising a trivalent metal and three phenolate active materials.

The material wherein each of the three phenolate active materials is different from the other.

The material wherein two of the three phenolate active materials are different from a third of said phenolate active materials.

The material wherein each of the three phenolate active materials is the same.

The material wherein one or more of the phenolate active materials is a therapeutic, cosmetic or veterinary material.

The material wherein one or more of the phenolate active materials is an agricultural material.

The material when comprising one or more phenolate active material and one or more non-active phenolate material.

The material wherein the phenolate active material is selected from cannabinoids, fenoldopam, tyrosine, xylenol, thymol, propofol, apomorphine, morphine and derivatives thereof, mitoxantrone, dexorubicine, hexachlorophene, acetaminophen, p-coumaric acid, 3,4-dihydroxybenzoic acid, 4-hydroxybenzoic acid, butylparaben, vanillic acid, guaiacol, caffeic acid, tolterodine, raloxifea, scopoletin, decursinol, dopamine, L-DOPA, curcumin, tianine and polyphenols.

The material wherein the active drug entity is a cannabinoid material.

The material wherein the cannabinoid material is selected amongst tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE) and cannabicitran (CBT).

The material wherein the cannabinoid is THC or CBD and chemical derivatives thereof.

The material wherein the phenol active material is selected from Salcaprozate sodium (SNAC), Tapinarof and materials from cinnamon extract.

The material wherein the phenol active material is a phytomaterial.

The material wherein the phenol active material is selected from mesalazine, salbutamol, pirbuterol, capsaicin, salmeterol, vilanterol, balsalazide, labetalol, mycophenolic acid, pyridoxine, phenylephrine, edrophonium, paracetamol, monobenzone, tapentadol, metaraminol, metirosine, oxymetazoline, nabilone, diflunisal, olsalazine, liothyronine sodium, desvenlafaxine, rotigotine, phentolamine, oxyphenbutazone, amodiaquine, olodaterol, troglitazone, eltrombopag, ivacaftor, indacaterol, cefadroxil, cefprozil, tetrahydrocannabinol, estradiol, estradiol valerate, estradiol cypionate, levallorphan, oxymorphone, nalbuphine, buprenorphine, butorphanol, naloxone, levorphanol, naltrexone, dezocine, morphine, naloxegol, methylnaltrexone, nalmefene, metacycline, sarecycline, omadacycline, eravacycline, equilin, flutemetamol, diethylstilbestrol, dienestrol, probucol, mitoxantrone, bazedoxifene, raloxifene, arbutamine, dobutamine, masoprocol, cannabidiol, terbutaline, orciprenaline, denoldopam, norepinephrine, corbadrine, isoprenaline, isoetarine, droxidopa, carbidopa, protokylol, apomorphine, entacapone, tolcapone, idarubicin, daunorubicin, doxorubicin, epirubicin and valrubicin.

A material comprising at least one cannabinoid in a form of a phenolate and a cation selected from metal cations, phosphonium and ammonium.

The material wherein the metal cation is a monovalent, divalent or trivalent metal atom.

The material wherein the metal cation is a divalent or trivalent cation.

The material wherein the metal cation is not a monovalent cation.

The material when comprising a divalent metal atom and one or two cannabinoids.

The material when comprising one cannabinoid and one non-cannabinoid.

The material when comprising a trivalent metal atom and one or two or three cannabinoids.

The material when comprising one cannabinoid and two non-cannabinoids.

The material when comprising two cannabinoids and one non-cannabinoid.

The material wherein the cannabinoid is CBD or THC.

The material wherein the metal cation is selected from lithium, sodium, potassium, calcium, magnesium, manganese, aluminum, zinc, nickel, iron, silver, gold barium metal cations.

The material wherein the metal cation is sodium or calcium.

A calcium CBD salt comprising one CDB and optionally another non-cannabinoid or two CBDs.

The material wherein the ammonium is an optionally substituted ammonium cation.

The material when comprising an optionally substituted ammonium cation and a phenolate active compound.

The material wherein the ammonium cation is a tetra-alkyl ammonium, optionally selected from tetramethylammonium, tetraethylammonium, tetrabutylammonium, tetrapentylammonium, tetrahexylammonium choline and choline derivatives.

A material being a cholate salt of at least one phenol active material.

The material wherein the active material is selected from cannabinoids, fenoldopam, tyrosine, xylenol, thymol, propofol, apomorphine, morphine and derivatives thereof, mitoxantrone, dexorubicine, hexachlorophene, acetaminophen, p-coumaric acid, 3,4-dihydroxybenzoic acid, 4-hydroxybenzoic acid, butylparaben, vanillic acid, guaiacol, caffeic acid, tolterodine, raloxifea, scopoletin, decursinol, dopamine, L-DOPA, curcumin, tianine and polyphenols.

The material wherein the active drug entity is a cannabinoid material.

The material wherein the cannabinoid material is selected amongst tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE) and cannabicitran (CBT).

The material wherein the cannabinoid is THC or CBD and chemical derivatives thereof.

The material wherein the phenol active material is selected from Salcaprozate sodium (SNAC), Tapinarof and materials from cinnamon extract.

The material wherein the phenol active material is a phytomaterial.

The material wherein the phenol active material is selected from mesalazine, salbutamol, pirbuterol, capsaicin, salmeterol, vilanterol, balsalazide, labetalol, mycophenolic acid, pyridoxine, phenylephrine, edrophonium, paracetamol, monobenzone, tapentadol, metaraminol, metirosine, oxymetazoline, nabilone, diflunisal, olsalazine, liothyronine sodium, desvenlafaxine, rotigotine, phentolamine, oxyphenbutazone, amodiaquine, olodaterol, troglitazone, eltrombopag, ivacaftor, indacaterol, cefadroxil, cefprozil, tetrahydrocannabinol, estradiol, estradiol valerate, estradiol cypionate, levallorphan, oxymorphone, nalbuphine, buprenorphine, butorphanol, naloxone, levorphanol, naltrexone, dezocine, morphine, naloxegol, methylnaltrexone, nalmefene, metacycline, sarecycline, omadacycline, eravacycline, equilin, flutemetamol, diethylstilbestrol, dienestrol, probucol, mitoxantrone, bazedoxifene, raloxifene, arbutamine, dobutamine, masoprocol, cannabidiol, terbutaline, orciprenaline, denoldopam, norepinephrine, corbadrine, isoprenaline, isoetarine, droxidopa, carbidopa, protokylol, apomorphine, entacapone, tolcapone, idarubicin, daunorubicin, doxorubicin, epirubicin and valrubicin.

A formulation selected from a pharmaceutical, cosmetic, veterinary or agricultural formulation, the formulation comprising an isolated material according to the invention.

The formulation as a pharmaceutical formulation adapted for topical, transdermal, oral, aerosol, parenteral, subcutaneous, intravenous, intramuscular, intraperitoneal, rectal or vaginal administration.

The formulation when comprising between 0.1 and 99% of said isolated material.

Use of at least one material according to the invention in the preparation of a formulation.

Use of at least one material according to the invention in a method of prophylaxis or treatment of at least one disorder or disease state.

A method of preparing a material according to the invention, the method comprising treating at least one phenol-containing active material with a base elected from metal containing base and an ammonia or an equivalent thereof.

The method wherein the base is selected from a metal hydride, a metal alkoxide, an alkali metal hydroxide, an alkaline earth metal hydroxide, a metal carbonates, a metal carbanion or a metal amide.

The method wherein the base is selected from NaOH, Ca(OH)2, Cu(OH)2, CaCl2, FeCl3, Zn(OH)2 and NaH.

A method of preparing a material according to the invention, the method comprising treating at least one phenol-containing active material with a base elected from a metal containing base and an ammonia or an equivalent thereof to obtain the material and treating said material under conditions enabling exchange of a counterion.

A material according to the invention, prepared by a method of the invention.

A material in the form of a multimolecular material comprising two or more phenol-containing active materials, each being ionically associated with a cation; wherein the cation is a multivalent metal cation or a poly-ammonium.

The material wherein the multivalent metal cation is a divalent, a trivalent or a tetravalent cation.

The material when formed by a reaction of a polyphenol with the multivalent cation or poly-ammonium.

The material for use in the preparation of nanoparticles or microparticles.

The material for use in the preparation of a coating material.

A particle comprising a material according to the invention.

The particle is a micro or a nano particle.

The particle wherein the material comprising polyphenols from green tea extract.

The particle wherein the material comprising tannic acid.

A material in the form of a multimolecular material comprising two or more phenol-containing materials, each being ionically associated with a cation; wherein the cation is a multivalent metal cation or a poly-ammonium.

The material wherein the multivalent metal cation is a divalent, a trivalent or a tetravalent cation.

The material when formed by a reaction of a polyphenol with the multivalent cation or poly-ammonium.

The material for use in the preparation of nanoparticles or microparticles.

The material for use in the preparation of a coating material.

A particle comprising a material according to the invention.

Use of a material being in a form of a metal or ammonium material of at least one phenol-containing material according to the invention for treating, ameliorating or preventing a disease or disorder found to be treatable by the material.

Use of at least one material according to the invention for the preparation of a formulation, a pharmaceutical composition or a medicament for treating, preventing or ameliorating a disease or a disorder found to be treatable by such formulation/composition/medicament.

Use of at least one material according to the invention for the preparation of a formulation, for protecting and treating plants and crops from bacterial and/or fungal infections.

The use wherein the material is selected from sodium chlorite, copper salicylate, bromochlorodimethylhydantoin, copper thymol, and polyguanidine.

The use wherein the bacterial and/or fungal infection is selected from *erwinia, pythium, Macrophomina phaseolina, athelia rolfsii* and potato scab.

A composition or a formulation comprising a material, wherein the material comprising a polyvalent metal cation having a valency of at least ($^{2+}$) and at least one active phenol-containing material in a form of a phenolate, ionically bonded to the polyvalent metal cation, wherein the composition or the formulation is for use in treating a disease or disorder which is treatable by administering to a subject a therapeutically effective amount of the composition or the formulation.

A composition or a formulation comprising a material, wherein the material comprising an ammonium cation or a poly-ammonium, and at least one active material comprising at least one phenolate moiety ionically bonded to the ammonium or the poly-ammonium cation, wherein the composition or the formulation is for use in treating a disease or disorder which is treatable by administering to a subject a therapeutically effective amount of the composition or the formulation.

DETAILED DESCRIPTION OF EMBODIMENTS

CBD metal complexes are formed according to a variety of procedures. Here, we apply only the most ambient reaction conditions in order to prevent unwanted side-reactions, particularly the chemical modification of CBD. Relative amounts of metal reagent were adjusted based on the metal valence, always kept to ensure the presence of enough metal ions to complex both available phenols in CBD.

Example 1: CBD-Salts Synthesis and Analysis

Na salt: A solution of NaOH (9.4 mg, 0.24 mmol) in ethanol (3.0 mL) was added to a stirred solution of CBD (35 mg, 0.11 mmol) in ethanol (5.0 mL). The mixture was stirred at room temperature for 1 h and solvent was evaporated, affording CBD-Na in quantitative yield.

CBD metal complexes were characterized by the following analytical techniques:

1) $^{1}H$ and $^{3}C$ Nuclear magnetic resonance (NMR)
2) Infrared spectroscopy (IR)
3) Thin-layer chromatography (TLC)
4) Differential scanning calorimetry (DSC)
5) Melting point (MP)
6) Elemental analysis
7) Ultraviolet absorption spectroscopy (UV)

Each method of characterization confirms an aspect of a successful synthesis:

NMR spectroscopy confirmed that reaction conditions did not disrupt any other part of the molecule, and that CBD structure is maintained, IR spectroscopy identified new functional groups, especially phenol-metal complexes, TLC confirmed consumption of starting material, and presence of new material based on differences in polarity, Melting point confirmed purity of the new substance, Elemental analysis confirmed that the CH % in the product is reduced due to the weight contribution of the metal content.

UV displayed a change in the absorption spectrum of the phenol ring

Results: A variety of CBD-metal complexes have been synthesized with mono-, di-, and tri-valent metal centers. Complexes formed either by reactions with metal hydroxides or salts such as chloride or sulfate (Method 1), or with metal hydrides under anhydrous conditions (Method 2).

CBD-Na Synthesis

A solution of NaOH (9.4 mg, 0.24 mmol) in ethanol (3.0 mL) was added to a stirred solution of CBD (35 mg, 0.11 mmol) in ethanol (5.0 mL). The mixture was stirred at rt for 1 h and solvent was evaporated, affording CBD-Na in quantitative yield.

CBD-K Synthesis

A solution of KOH (2.5 mg, 0.045 mmol) in methanol (2.5 mL) was added to a stirred solution of CBD (7.1 mg, 0.023 mmol) in methanol (2.5 mL). The mixture was stirred at rt for 1 day and solvent was evaporated, affording CBD-K in quantitative yield.

CBD-Ca Synthesis

A solution of $CaCl_2$ (5.2 mg, 0.046 mmol) in methanol (2.5 mL) was added to a stirred solution of CBD (7.3 mg, 0.023 mmol) in methanol (2.5 mL). The mixture was stirred at rt for 1 day and solvent was evaporated, affording CBD-Ca.

CBD-Cu Synthesis

A solution of $CuSO_4$ (7.2 mg, 0.045 mmol) in methanol (2.5 mL) was added to a stirred solution of CBD (9.2 mg, 0.029 mmol) in methanol (2.5 mL). The mixture was stirred at rt for 1 day and solvent was evaporated, affording CBD-Cu.

CBD-Zn Synthesis

A solution of $ZnCl_2$ (2.5 mL of a 0.8 mg $mL^{-1}$ solution) was added to a stirred solution of CBD (5.2 mg, 0.017 mmol) in methanol (2.5 mL). The mixture was stirred at rt for 1 day and solvent was evaporated, affording CBD-Zn in quantitative yield.

CBD-Al Synthesis

A solution of $AlCl_3$ (3.1 mg, 0.011 mmol) in methanol (5 mL) was added to a stirred solution of CBD (5 mg, 0.016 mmol) in methanol (2.5 mL). The mixture was stirred at rt for 1 day and solvent was evaporated, affording CBD-Al in quantitative yield.

CBD-Fe Synthesis

A solution of $FeCl_3$ (9.2 mg, 0.057 mmol) in ethanol (3 mL) was added to a stirred solution of CBD (24.1 mg, 0.077 mmol) in ethanol (5 mL). The mixture was stirred at rt for 1 day and solvent was evaporated, affording CBD-Fe in quantitative yield.

Example 2: Preparation of CBD Salts be the Reaction with Metal Hydrides or Ethoxides Sodium hydride (50% in oil, 2.3 mg, 0.096 mmol) was washed (3×1 mL) and finally covered with THF (5 mL) under argon. CBD (15 mg, 0.048 mmol) was then added and the mixture was allowed to stir for 0.5 h. The mixture was diluted with ether (10 mL) and washed with 10% NaOH (3×5 mL). Combined organic extracts were dried over $Na_2SO_4$ and solvent was evaporated affording CBD-Na in quantitative yield.

Reaction of CBD with Sodium Ethoxide to Obtain CBD-Na

The CBD-Na complex may also be synthesized with sodium metal in ethanol. Sodium (2.2 mg, 0.096 mmol) was added to a solution of CBD (15 mg, 0.048 mmol) in ethanol (5 mL). The mixture was stirred for 0.5 h, diluted with ether (10 mL) and washed with 10% NaOH (3×5 mL). Combined organic extracts were dried over $Na_2SO_4$ and solvent was evaporated affording CBD-Na in quantitative yield.

Analysis of CBD Metal Complexes

Synthesis of CBD metal complexes was first indicated by thin-layer chromatography (TLC) with silica as the stationary phase and a 9:1 mixture of hexane:ethyl acetate as the mobile phase. Plates were visualized under UV light (254 nm) Metal complexes were compared to CBD (Rf=0.69) and displayed increased polarity (Rf=0).

NMR studies show that CBD maintained its structural integrity through these reaction conditions, displaying nearly identical H NMR spectra before and after synthesis. The phenolic proton disappear and the aromatic protons of the phenol shifted.

CBD metal complexes were tested for water solubility (Table 1). Significantly, sodium, calcium and copper complexes were all soluble at 10 mg/mL. CBD plant extract is only soluble at 0.0126 mg/mL.

TABLE 1

Water solubility of CBD metal complexes.

| CBD Metal Complex | Solubility in water |
|---|---|
| CBD-Na | 10 mg/mL |
| CBD-K | 2 mg/mL |
| CBD-Ca | 10 mg/mL |
| CBD-Cu | 10 mg/mL |
| CBD-Zn | 1.7 mg/mL |
| CBD-Al | 2 mg/mL |
| CBD-Fe | 1.4 mg/mL |

Reversibility

1M HCl solution was added dropwise to aqueous solution of CBD-Na until pH of 3 was achieved. Immediate appearance of an insoluble brown oil was observed in the mixture, which was confirmed by $^1H$ NMR to be CBD. The ease of reversibility is paramount to the success of this work, as original compounds may be easily reconstituted by a simple chemical process.

Thermal Properties

The thermal properties of CBD-Na were compared to CBD by Differential Scanning Calorimetry (DSC). DSC was performed under a nitrogen flow of 60 mL $min^{-1}$ at a scan rate of 10° C. $min^{-1}$ from 25 to 100° C., showing the thermal behavior of the metal complex and the parent molecule throughout this temperature range. The melting point of the CBD-Na metal complex was found to be 55° C., compared to the observed melting point of 66° C. for the parent CBD molecule.

Preparation of Metal Complexes Using Metal Hydrides

CBD ionic complexes were performed with metal hydrides (NaH, $CaH_2$) in order to afford complexes with no side products. A solution of CBD (35 mg, 0.11 mmol) in DCM (1 mL) was added to a dispersion of excess NaH/$CaH_2$ in DCM (1 mL) under dry argon gas. The mixture was left to mix at room temperature overnight. Bubbling was observed in the reaction mixture, related to the formation and release of hydrogen. The solvent was evaporated to afford CBD-Na/Ca. Products were confirmed by TLC in 9:1 hexane/ethyl acetate ($R_f$=0) and spectral analysis. The appearance of the product resembled that of ionic complexes formed by reaction with metal chlorides or hydroxides.

Preparation of Metal Complexes Using Sodium Ethoxide

CBD ionic complexes were performed with sodium ethoxide in order to afford complexes with no side products. A solution of CBD (35 mg, 0.11 mmol) in ethanol (1 mL) was added to a sodium ethoxide solution prepared by adding sodium metal to ethanol (1 mL) under dry argon gas. The mixture was left to mix at room temperature for 30 minutes. The solvent was evaporated to afford CBD-Na. Products were confirmed by TLC in 9:1 hexane/ethyl acetate ($R_f$=0) and spectral analysis. The appearance of the product resembled that of ionic complexes formed by reaction with metal chlorides or hydroxides.

Oxidation Stability

A solution of CBD in ethanol was exposed to air bubbled through and sun light. A decrease in CBD content was recognized after 24 hours of exposure. When the CBD metal complexes were exposed to air bubbled through oxidation and sun light for 24 hours, no change in CBD content is found, as determined by HPLC.

CBD Metal Material Formation

Divalent metal-CBD complexes are synthesized using different divalent metal hydroxides such as $Ca(OH)_2$ and $Ba(OH)_2$ using the following procedure.

CBD (1 equiv.) and divalent metal hydroxide (1 equiv.) are taken in a reaction vial with magnetic bar. The reaction vial is kept under Argon atmosphere. Then ethanol:water (1:1) mixture is added and the reaction mixture is stirred at RT. The completion of the reaction is monitored by TLC. After the completion of reaction, ethanol is removed using vacuum. The water is removed using lyophilizer, which yields the divalent metal-CBD complexes as a solid.

Ca-CBD complex: CBD (100 mg, 0.32 mmol, 1 equiv.) and calcium hydroxide (24 mg, 0.32 mmol, 1 equiv.) were taken in a 4 mL reaction vial with magnetic bar. Subsequently, 3 mL of ethanol:water (1:1) mixture was added. The reaction vial was kept under argon atmosphere. Then the reaction mixture was stirred at RT. The TLC was checked using 10% ethyl acetate/n-hexane solution as an eluent. After the consumption of CBD (~48 h), which confirmed by TLC, the ethanol was removed using vacuum. The resulting complex was lyophilized for overnight, which yields the product as a dark violet color solid. The obtained solid product was analyzed using FT-IR and NMR.

Ba-CBD complex: CBD (100 mg, 0.32 mmol, 1 equiv.) and barium hydroxide pentahydrate (101 mg, 0.32 mmol, 1 equiv.) were taken in a 4 mL reaction vial with magnetic bar. Subsequently, 3 mL of ethanol:water (1:1) mixture was added. The reaction vial was kept under Ar atmosphere. Then the reaction mixture was stirred at RT. The TLC was checked using 10% ethyl acetate/n-hexane solution as an eluent. After the consumption of CBD (~48 h), which confirmed by TLC, the ethanol was removed using vacuum. The resulting complex was lyophilized for overnight, which yields the product as a dark violet color solid. The obtained solid product was analyzed using FT-IR and NMR.

Generally, CBD is soluble in ethanol but not soluble in water. However, $Ca(OH)_2$ and $Ba(OH)_2$ are not soluble in ethanol and slightly soluble in water. Thus, ethanol:water (1:1) mixture was used for the reaction of divalent metal-CBD reaction. When the CBD and $Ca(OH)_2/Ba(OH)_2$ was stirred in ethanol:water (1:1) mixture at room temperature (rt), white color partially dissolved solution was observed. When reaction proceeds, the color of the solution gradually changed to dark violet and finally dark violet color solid was obtained after evaporation of the solvent.

NMR Analysis of Divalent Metal-CBD Complexes

1H NMR spectrum of CBD and Ba-CBD complex was obtained. The intensity of the peak at 6.01 ppm that corresponds to two aromatic C—H protons of CBD is almost disappeared and a new peak appeared at 6.15 ppm in the Ca-CBD complex. In addition, the peak at 8.66 ppm that attributes to two OHs of CBD is vanished in the Ca-CBD complex.

Similarly, for Ca-CBD salt, the intensity of the peak at 6.01 ppm that corresponds to two aromatic C—H protons of CBD is decreased and new peaks were observed nearby in the Ca-CBD complex. In addition, the intensity of the peak at 8.66 ppm that attributes to two OHs of CBD is decreased and new peaks were noticed in the vicinity in the Ca-CBD complex.

Characterization of CBD-Na Derivatives

The synthesized CBD-Na derivatives were characterized by 1H NMR and FTIR spectra. A new peak is appearing at 6.99 ppm in case of CBD-Na (synthesized using NaH) which supports the formation of phenolate anion in CBD. Since CBD contain two phenol groups, a mono or disodium salts may be formed.

The FTIR spectrum also supports the formation of sodium derivative of CBD. The hydrogen bonded peak of —OH groups at 3425 cm-1 of CBD is suppressed and shifted to 3420 cm-1 for CBD-Na (synthesized using NaH), due to formation of metal derivative of CBD. The peaks at 1628 cm-1 and 1582 cm-1 of CBD are also shifted to 1643 cm-1 and 1514 cm-1 in CBD-Na.

Characterization of CBD-Ca Derivatives

The synthesized CBD-Ca derivative was characterized by 1H NMR and FTIR spectra. A new peak is appearing at 6.97 ppm in case of CBD-Ca which supports the formation of phenolate anion in CBD. The FTIR spectrum also supports the formation of calcium derivative of CBD. The hydrogen bonded peak of —OH groups at 3425 cm-1 of CBD is suppressed and a sharp peak of non-hydrogen bonded —OH groups is appeared at to 3640 cm-1 for CBD-Ca, due to formation of metal derivative of CBD and breaking of inter molecular hydrogen bonding of CBD.

Example 3: Synthesis and Characterization of CBD-Fe Derivatives

Synthesis: In a nitrogen purged round bottom flask, 200 mg of CBD (0.63 mmol) was dissolved in 20 ml of ethanol. $FeCl_3$ (34 mg, 0.21 mmol), dissolved in 10 ml dehydrated ethanol, was added to the CBD solution. The solution was kept for staring in room temp for 24 h.

The EDX spectra of CBD-Fe confirms the presence of the elements C, O, Fe and Cl and the atomic % is 82 for carbon and 2.17 for Fe. So, the ratio of C and Fe is ~38:1. In case of exactly replacement of the two-chloride ion by phenolic —OH group of CBD, this ration should be ~42:1. This result confirms the formation of $CBD_2FeCl$.

The FTIR spectrum also supports the formation of iron derivative of CBD. The hydrogen bonded peak of —OH groups at 3425 cm-1 of CBD is suppressed and shifted to 3300 cm-1 for CBD-Fe, due to formation of metal derivative of CBD. The peak at 1628 cm-1 of CBD, assigned to bending vibration modes of —OH group is also suppressed and shifted to 1621 cm-1 in CBD-Fe. The strong aromatic bands at 1582 cm-1 and 1442 cm-1 of CBD shifted to 1576 cm-1 and 1426 cm-1 in CBD-Fe salt indicates the change in the aromatic C═C bonds, which shows the conversion of CBD to CBD-Fe.

The DSC study shows that pure has a peak at 69° C. whereas CBD-Fe shows major peak at 132.69° C. with also a small peak at 64° C.

For all salts, adding acidic solution such as HCl, convert back the native CBD.

Example 4: Reaction of CBD with Various Monovalent Metal Salts

CBD reaction with NaOH, $Na_2CO_3$ or $NaHCO_3$: In nitrogen purged round bottom flask, 25 mg of CBD was dissolved in 3 ml of methanol. Then 17 mg of $Na_2CO_3$ or the equivalent of sodium hydrogen carbonate and NaOH. in 2 ml ethanol, was added to the CBD solution. The solution was kept for staring in room temp for 24 h. The final dried mixture contains two portions. One is soluble in water; another portion is insoluble in water. NMR, FTIR and MS of both the two portions were checked. The water-soluble portion contain sodium salt CBD and a compound which might be oxidized CBD. The water insoluble portion contain either unreacted CBD or a single sodium salt.

CBD reaction with Using NaCl: 20 mg of CBD was dissolved in 3 ml of dehydrated ethanol. Then 8.8 mg of NaCl dissolved in 2 ml dehydrated ethanol was added to the CBD solution. The solution was stirred in room temp for 72 h. No reaction, CBD remain intact, no water-soluble compound.

Similar results were obtained when using KOH, LiOH, LiCl, KCl, $KHCO_3$ and $K_2CO_3$ under similar conditions where the KCl and LiCl did not react with CBD while the base compounds formed the corresponding CBD salt but as a mixture with CBD and probably as oxidized CBD.

CBD reaction with $ZnCl_2$: CBD (100 mg, 0.32 mmol, 1 equiv.) and zinc chloride (44 mg, 0.32 mmol, 1 equiv.) were taken in a 4 mL reaction vial with magnetic bar. Subsequently, 3 mL of ethanol:water (1:1) mixture was added. The reaction vial was kept under Ar atmosphere. Then the reaction mixture was stirred at RT. The TLC was checked using 10% ethyl acetate/n-hexane solution as an eluent. After the consumption of CBD, as confirmed by TLC, the ethanol was removed using vacuum. The resulting salt was lyophilized overnight to yield the product as a solid.

CBD reaction with $MgCl_2$: CBD (100 mg, 0.32 mmol, 1 equiv.) and magnesium chloride (31 mg, 0.32 mmol, 1 equiv.) were taken in a 4 mL reaction vial with magnetic bar. Subsequently, 3 mL of ethanol:water (1:1) mixture was added. The reaction vial was kept under Ar atmosphere. Then the reaction mixture was stirred at RT. The TLC was checked using 10% ethyl acetate/n-hexane solution as an eluent. After the consumption of CBD, as confirmed by TLC, the ethanol was removed using vacuum. The resulting salt was lyophilized overnight to yield the product as a solid.

TLC was checked to confirm the completion of the reactions. After 24-48 h of the reaction, the complete consumption of CBD was observed. Divalent metal-CBD complexes were observed at the baseline of the TLC. TLC and H NMR spectra indicated that the metal salt is obtained with some side products (single metal or dimers) are formed.

Reaction of CBD and $FeCl_3$: CBD (58.7 mg, 0.187 mmol) and iron (III) chloride (20.4 mg, 0.126 mmol) were taken in anhydrous ethanol (6 mL) and stirred at rt overnight. Solvent was evaporated to near dryness, and then precipitated into pentane. The pentane fraction contained only CBD, and a precipitate was collected. 1H NMR was unattainable due to presence of paramagnetic iron (III), and so the sample was characterized by gel-permeation chromatography (GPC). The observed MW of 1950 indicated presence of several (~6) CBD units in a complex. The product was then taken up in ethanol/0.1 M HCl (2:1 ratio), and the resulting precipitate was the starting CBD. The same reaction was performed in THF which formed the Fe-complex that was converted back to CBD when acidifying with HCl. Differed complexes were obtained when reacting $FeCl_3$ with CBD at different ratios and reaction conditions.

Reaction of CBD and $Al(Cl)_3$: CBD (106 mg, 0.337 mmol) and anhydrous aluminum chloride (35.2 mg, 0.264 mmol) were taken in anhydrous ethanol (15 mL) and stirred at rt overnight. Solvent was evaporated to dryness, and the crude product was washed with chloroform to remove unreacted CBD. 1H NMR displayed a shift of aromatic proton peaks, indicating complex formation. The product was then taken up in ethanol/0.1 M HCl (2:1 ratio), and the resulting precipitate was shown to be CBD.

Example 5: Synthesis of Ammonium-CBD Complex Using Ammonium Hydroxide

Ammonium-CBD complexes were synthesized using a series of ammonium hydroxides such as tetramethylammonium-, tetraethylammonium-, tetrabutylammonium-tetrapentylammonium- or tetrahexylammonium hydroxides using the following procedure (Scheme 7):

CBD (1 equiv.) solution in ethanol was mixed with a solution of tetra-butylammonium hydroxide (2 equiv.) in ethanol. The reaction mixture was stirred at room temperature overnight where ethanol was evaporated to yield the ammonium-CBD complex.

Example 6: Synthesis of Ammonium-Fenoldopam Using Ammonium Hydroxide

Ammonium-fenoldopam complexes was synthesized using a series of ammonium hydroxides, including tetraethylammonium, tetrabutylammonium and choline. Fenoldopam mesylate (1 equiv.) in ethanol:water (1:1) mixture was mixed with a solution of tetra-alkylammonium hydroxide (3 equiv.) in ethanol:water (1:1) mixture and stirred at room temperature. The completion of the reaction was monitored by TLC. After solvent evaporation, ammonium-fenoldopam complex was obtained.

Example 7: Synthesis of Ammonium-CBD Complex Using Ammonium Hydroxides

Synthesis of ammonium hydroxide: Various amines such as trimethylamine, triethylamine, tributylamine, trihexylamine, N-methylpyrrolidine and N-methylpiperidine were converted to the ammonium hydroxide derivatives using the following procedure. This allows to synthesis diverse series of ammonium-phenolate complexes.

In first step, tetra-alkyl substituted ammonium bromides/iodides was synthesized by the alkylation of amine (1 equiv.) with the corresponding alkyl halide (1 equiv.) in acetonitrile. The reaction mixture was stirred vigorously at a temperature of 75° C. for 12 h to form a solid product that was filtered and washed thoroughly with hexane to obtain the pure tetra-alkyl substituted ammonium halides.

These synthesized and other commercially available ammonium halide derivatives were converted to the ammonium hydroxide derivatives using the following procedure.

Tetra ammonium bromide/iodide (1 equiv.) in ethanol was mixed with a solution of KOH (1 equiv.) in ethanol and heated gradually to 60° C. overnight. The KBr precipitate was removed by filtration to yield the tetra-alkylammonium hydroxide solution. The solvent was removed by evaporation to yield tetra-alkylammonium hydroxide.

Preparation of CBD-ammonium salts: CBD (100 mg, 0.32 mmol, 1 equiv.) was taken in a 4 mL reaction vial with magnetic bar. The reaction vial was kept under Ar atmosphere. Then 1 mL ethanol was added and stirred to dissolve the CBD. Afterwards, a solution of tetramethylammonium hydroxide pentahydrate (115 mg, 0.64 mmol, 2 equiv.) or tetrabutylammonium hydroxide (40% solution in water, 414 μL, 0.64 mmol, 2 equiv.) dissolved in 1 mL ethanol was added by dropwise. Then the reaction mixture was stirred at RT. The TLC was checked using 10% ethyl acetate/n-hexane solution as an eluent. After the consumption of CBD, which confirmed by TLC, the ethanol was removed using vacuum. The resulting salt was lyophilized for overnight, which yields the product as a solid. The obtained solid product was analyzed using FT-IR, UV, and NMR.

Synthesis of ammonium-CBD complex using ammonium halides: Tetraethylammonium bromide (3.15 g, 15 mmol, 1 equiv.) or tetrapentylammonium bromide (5.68 g, 15 mmol, 1 equiv.) or tetrahexylammonium iodide (7.22 g, 15 mmol, 1 equiv.) was taken in a 50 mL round bottom flask equipped with a magnetic bar. A solvent, ethanol (10 mL) was added and the mixture was stirred to dissolve tetra ammonium bromide/iodide. After a clear solution was observed, a solution of KOH (0.84 g, 15 mmol, 1 equiv.) dissolved in ethanol was added. Then the mixture was heated gradually to 60° C. After 24 h, the mixture was cooled to room temperature. Afterwards KBr precipitate was removed by filtration, which yields the tetra-alkylammonium hydroxide solution. The solvent was removed by evaporation that gave tetra-alkylammonium hydroxide.

CBD (100 mg, 0.318 mmol, 1 equiv.) was taken in a 4 mL reaction vial with magnetic bar. The reaction vial was kept under Ar atmosphere. Then 1 mL ethanol was added and stirred to dissolve the CBD. Afterwards, a solution of tetraethylammonium hydroxide (94 mg, 0.636 mmol, 2 equiv.) or tetrapentylammonium hydroxide (201 mg, 0.636 mmol, 2 equiv.) or tetrahexylammonium hydroxide (236 mg, 0.636 mmol, 2 equiv.) dissolved in 1 mL ethanol was added by dropwise. Then the reaction mixture was stirred at RT. The TLC was checked using 10% ethyl acetate/n-hexane solution as an eluent. After the consumption of CBD, which confirmed by TLC, the ethanol was removed using vacuum. The resulting salt was lyophilized for overnight, which yields the product as a solid. The obtained solid product was analyzed using FT-IR, UV, and NMR.

Synthesis of ammonium-CBD complexes: CBD exhibits pale brown color clear solution in ethanol. When, this solution added with the solution of tetrabutylammonium- and tetramethylammonium-hydroxide in ethanol, when reaction proceeds the color of the solution gradually changed to dark violet. The TLC was checked to confirm the completion of the reaction. After 48 h of the reaction, the complete consumption of CBD was observed. The ammonium-CBD complex was observed at the bottom. However, three other spots were observed in TLC.

FT-IR analysis of ammonium-CBD complexes: FT-IR spectrum of CBD and their tetramethylammonium and tetrabutylammonium complexes exhibit significant change in their frequencies. The change in the strong bands at 1582 $cm^{-1}$ and 1442 $cm^{-1}$ of CBD to 1514 $cm^{-1}$ in ammonium-CBD complexes indicates the change in the aromatic C═C bonds, which shows the conversion of CBD. In addition, the disappearance of the frequencies at 1628 $cm^{-1}$ indicates change in the double bonds of CBD.

NMR analysis of ammonium-CBD complexes: H NMR spectrum of CBD, ammonium hydroxide, and ammonium-CBD complexes were compared. The peak at 6.18 ppm and 5.97 ppm that corresponds to two OHs of CBD is disappeared in the ammonium-CBD complexes. In addition, methyl and butyl protons of the respective ammonium hydroxides are incorporated in the ammonium-CBD complexes. However, due to the involvement of the double bonds of CBD, side reactions were observed in the NMR spectrum. Also oxidized product of CBD was observed. The compound can be further purified by washing with suitable solvents or column chromatography.

UV analysis of ammonium-CBD complexes: UV analysis of ammonium-CBD complexes compared with CBD was carried out. CBD or ammonium-CBD complexes in ethanol (20 μg/mL) was analyzed for UV. CBD shows absorptions at 229-235 nm and 274-281 nm. These absorptions are widened and shifted in ammonium-CBD complexes.

Example 8: Synthesis of Ammonium-Fenoldopam Complex Using Ammonium Hydroxides Fenoldopam mesylate (50 mg, 0.12 mmol, 1 equiv.) was taken in a 4 mL reaction vial with magnetic bar. The reaction vial was kept under Argon atmosphere. Then, 1 mL ethanol: water (1:1) mixture was added and stirred to dissolve the fenoldopam mesylate. Afterwards, a solution of tetramethylammonium hydroxide pentahydrate (68 mg, 0.36 mmol, 3 equiv.) or tetrabutylammonium hydroxide (40% solution in water, 243 μL, 0.36 mmol, 3 equiv.) dissolved in 1 mL ethanol:water (1:1) mixture was added by dropwise. Then the reaction mixture was stirred at RT. After the consumption of CBD, which confirmed by TLC, the ethanol was removed using vacuum. The water was removed using lyophilizer overnight, which yields the product as a solid. The obtained solid product was analyzed using FT-IR, UV, and NMR.

Synthesis of ammonium-fenoldopam complexes: Fenoldopam mesylate exhibits colorless solution in ethanol: water (1:1) mixture. When, this solution added with the solution of tetramethylammonium- or tetrabutylammonium-hydroxide in ethanol:water (1:1) mixture turns to pale green color solution. After completion of the reaction, tetramethylammonium- and tetrabutylammonium-hydroxide reactions convert to dark brown color and dark brown color solid respectively.

$^1$H NMR spectrum of fenoldopam mesylate and tetrabutylammonium-fenoldopam complex were compared. The peak at 9.01 ppm, 8.94 ppm and 8.81 ppm that corresponds to three OHs of fenoldopam is disappeared in the tetrabutylammonium-fenoldopam complex. In addition, butyl protons of the tetrabutylammonium hydroxide are incorporated in the tetrabutylammonium-fenoldopam complex.

UV analysis of ammonium-fenoldopam complexes: UV analysis of ammonium-fenoldopam complexes compared with fenoldopam mesylate was performed. Fenoldopam or ammonium-fenoldopam complexes in ethanol (20 μg/mL) were analyzed by UV. Fenoldopam shows absorptions at 218 nm and 284 nm. These absorptions are widened and shifted in ammonium-fenoldopam complexes. In tetramethylammonium-fenoldopam complex, the absorption at 218 nm and 284 nm shifted to 229 nm and 280 nm respectively. Also, the new absorptions were observed at 306 nm and 338 nm. In tetrabutylammonium-fenoldopam complex, the absorption at 218 nm and 284 nm shifted to 226 nm and 279 nm respectively. Also, the new absorptions were observed at 308 nm and 331 nm.

Example 9: Synthesis, Formulation and Pharmacokinetics of CBD-Choline

CBD-choline salt was obtained as a dark violet color solid which is soluble in methanol, ethanol and DMSO, insoluble in toluene, hexane and chloroform, and sparingly soluble in water. CBD-choline was confirmed using NMR and FT-IR analyses. CBD was successfully regenerated from CBD-choline salt at pH-3. The methodology of CBD-choline salt was extended to other choline derivatives such as L-α-Phosphatidylcholine. CBD-choline is dispersed in aqueous media using self nano-emulsifying drug delivery system formulation, with particles of hydrodynamic diameter 85 nm and zeta potential −3.7 mV. The Log P 1.71 was determined in octanol/water. The CBD-choline salt was detected by HPLC-MS using the similar method used for CBD. The salt was extracted from acidified plasma in high yield.

CBD-Choline salt was synthesized using choline hydroxide (46% in water solution). CBD (1.0 equiv.) and choline hydroxide (2.2 equiv.) were stirred at RT under nitrogen atmosphere using methanol as a solvent. The completion of the reaction was monitored by TLC. After the completion of the reaction, methanol was removed under vacuum and lyophilized to yield CBD-Choline as a dark violet color solid.

CBD is soluble in methanol and forms pale brown color clear solution. When the solution of CBD in methanol was added dropwise to the solution of choline hydroxide in methanol, a dark violet color clear solution was observed. When reaction proceeds, the color of the solution intensifies into dark violet. The salt was isolated as dark violet solid, obtained after evaporation of the solvent.

Characterization: The $^1$H NMR spectrum of CBD-choline salt was compared with CBD in methanol-$d_4$. The peak at 6.08 ppm that corresponds to two aromatic C—H protons of CBD is shifted to 6.00 ppm in the CBD-choline salt. In addition, other protons of double bonds of CBD appeared at 5.28 ppm, 4.47 ppm and 4.43 ppm are shifted to 5.33 ppm, 4.51 ppm and 4.43 ppm in CBD-choline. The NMR study revealed that the formation of CBD-choline. IR spectra of CBD-choline CBD were compared. In CBD-choline, the aromatic frequencies observed in 1643 cm-1, 1622 cm-1 and 1581 cm-1 were shifted to 1640 cm-1 and 1561 cm-1 compare to CBD, which confirms the formation of the CBD-choline salt.

Regeneration of CBD from CBD-choline salt. To check the regeneration of CBD from CBD-choline salt, CBD-choline was added to a pH=3 solution and extracted with $CDCl_3$. The $CDCl_3$ layer clearly shows that the regeneration of CBD from CBD-choline salt, confirmed by $^1$H NMR.

A method has been developed for the detection of CBD-choline by HPLC-MS. A linear curve has been defined for concentrations ranging from 5 ng/mL-1 μg/mL. A linear relationship between peak AUC (y-axis) and CBD-choline concentration (x-axis) has been defined.

Synthesis of CBD-Choline salts: CBD-Choline salt was synthesized using choline hydroxide (46% in water solution) as shown in Scheme 7. CBD (1.0 equiv.) and choline hydroxide (2.2 equiv.) were stirred at RT under a nitrogen atmosphere using methanol as a solvent. The completion of the reaction was monitored by TLC. After the completion of the reaction, methanol was removed using a vacuum and dried using lyophilizer, which yields the CBD-Choline as a dark violet color solid.

Scheme 9

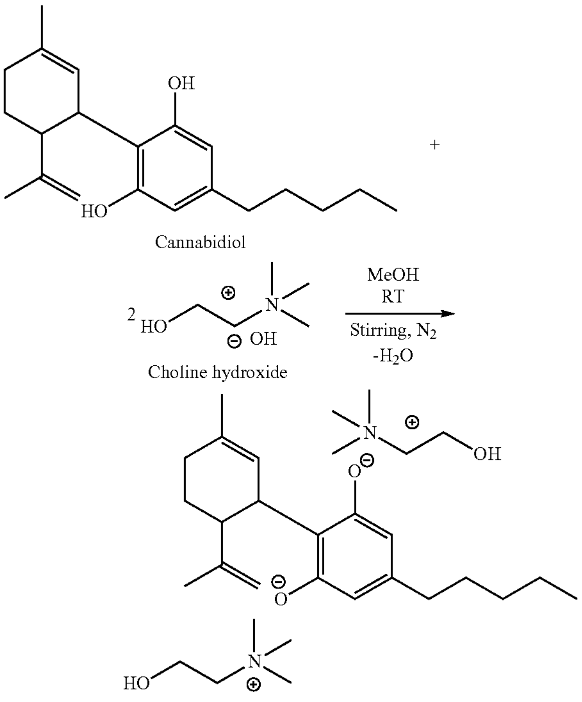

Cannabidiol

Choline hydroxide

CBD-Choline salt

Synthesis of Pure CBD Salts with High Regeneration to CBD:

The synthesis of pure CBD salts using easily removable side-products.

CBD-Na salt: CBD (300 mg, 0.953 mmol, 1 equiv.) was dissolved in 3 mL dry THF, then NaH (83 mg, 2.09 mmol, 2 equiv.) dissolved in 3 mL dry THF was added dropwise under the $N_2$ atmosphere over a period of 10 minutes. Afterwards, the reaction mixture was allowed for stirring at RT for 24 h under $N_2$ atmosphere. After completion of the reaction, black colour precipitate was formed in the reaction mixture, which was collected and purified by washing several times (10 mL×3) with n-heptane. The precipitate was collected and dried in a temperature controlled hot air oven. Yield: 260 mg (76%). The resulting CBD-Na salt was analyzed using FT-JR and NMR.

CBD-Choline (1:1) salt: Choline hydroxide solution (46% solution in water, 391 μL, 1.59 mmol, 1 equiv.) was taken in a 20 mL reaction vial. 10 mL methanol was added and vortexed to dissolve. Then, CBD (500 mg, 1.59 mmol, 1 equiv.) dissolved in 10 mL of methanol was added dropwise under nitrogen atmosphere. The reaction vial was closed tightly under nitrogen atmosphere and covered with aluminum foil. Then the reaction mixture was stirred at RT. The TLC was checked using 10% ethyl acetate/n-hexane solution as eluent. After the consumption of CBD (~48 h), which confirmed by TLC, the methanol was removed using a vacuum. The resulting salt was lyophilized overnight, which provided the CBD-Choline salt as a dark violet color solid that analyzed using FT-IR and NMR.

Modified synthesis of CBD salt and CBD recovery: CBD-Na salt was synthesized by modified procedure using CBD and NaH instead of NaOH as shown in Scheme 1. CBD (1.0 equiv.) and NaH (2.0 equiv.) are stirred at RT under a nitrogen atmosphere using dry THF as a solvent. After the completion of the reaction, the CBD-Na salt was collected and washed with n-heptane to remove unreacted CBD and other impurities.

Scheme 10

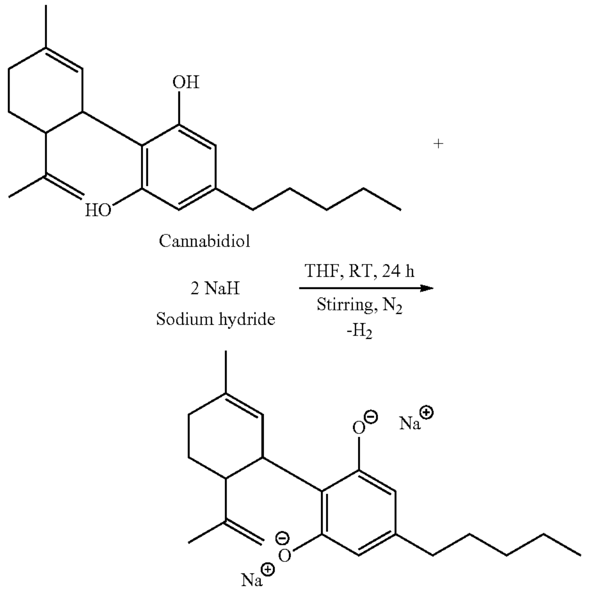

Cannabidiol

CBD-Sodium salt

NMR Analysis: Unlike pure CBD, the NMR spectra of CBD-Na did not show any phenolic OH resonances around at 8.6 ppm in the $^1$H-NMR spectra. This represents the formation of CBD-Na. Moreover, other aromatic and aliphatic resonances of the CBD-Na were shifted compared to the CBD.

IR-analysis: The FT-IR spectra of CBD-Na, was analysed with the comparison to CBD. CBD shows the FT-IR stretching frequencies for aromatic hydroxyl groups around at 3518 $cm^{-1}$ and 3406 $cm^{-1}$.These frequencies are disappeared in its analogue CBD-Na salt which confirms the conversion of aromatic hydroxyl groups into its corresponding CBD-Na salt. The alkane and alkene C—H starching frequency of these compounds were shown at 2931 $cm^{-1}$ and 2857 $cm^{-1}$ respectively. Most importantly, these compounds exhibited different aromatic C═C and C—O starching frequencies in the range 1643-1428 $cm^{-1}$ and 1251 $cm^{-1}$ respectively.

Synthesis, results, and analysis of CBD-Ch salt: CBD-Choline salt (1:1) was synthesized using CBD and choline hydroxide (46% in water solution) as shown in Scheme 10. CBD (1.0 equiv.) and choline hydroxide (1.0 equiv.) were stirred at RT under a nitrogen atmosphere using methanol as a solvent. The completion of the reaction was monitored by TLC. After the completion of the reaction, methanol was removed using a vacuum and dried using lyophilizer, which yields the CBD-Choline as a dark violet color solid.

NMR analysis of CBD-choline salt: $^1$H NMR spectrum was obtained in DMSO-$d_6$. The peak at 8.64 ppm that corresponds to phenolic OH disappeared in the CBD-choline salt. Other aromatic and double bond protons are shifted.

The peaks related to choline moiety is observed at 3.11 ppm for three $CH_3$ protons, 3.38 ppm and 3.81 ppm for two $CH_2$ protons and 5.52 ppm for OH proton.

HPLC analysis of regenerated CBD from CBD-Choline (1:1): Regeneration studies were performed for CBD-Choline salt (1:1) in the HCl solution (pH=1.0) followed by extracting of the free CBD using chloroform. The appropriate amount of the CBD-Choline salt (please see table 1 for details) was taken into the 5 mL vial, to this 2 mL of HCl solution (pH=1.0) was added. Few drops of con. HCl was added to make the solution pH=1.0. The resultant mixture was kept in a shaker for 30 min. After 30 min of acid treatment, 2 mL of chloroform was added to the reaction mixture (extraction was repeated for 3 times 3×2 mL) and vortexed for 15 min. The organic and aqueous layers were separated and dried using rotavapor followed by lyophilization for overnight. The weight of the CBD generated after acid treatment from CBD-Choline salt was measured by using weighing and HPLC studies. The results are given in Table 2. Interestingly, CBD-Choline (1:1) regenerates to CBD for about 67.0% HPLC according to the HPLC analysis.

TABLE 2

HPLC studies of the regenerated CBD from CBD-Choline (1:1) salt at pH = 1.0.

| Sample | Amount taken for regeneration study (mg) | Organic layer: Wt after evaporation (mg) | CBD by HPLC (mg) | CBD theoretical (mg) | CBD regenerat. (%) | Mol Wt |
|---|---|---|---|---|---|---|
| CBD-pure For comparison | 55.28 | 58.10 | 57.52 | 55.28 | 100.00 | 314.47 |
| CBD-Choline (1:1) salt | 61.42 | 44.98 | 30.99 | 46.25 | 67.01 | 417.63 |

Summary: CBD-Choline (1:1) salt regenerates to CBD with 67.01%; CBD-Na was successfully prepared using CBD and NaH; This methodology was applied to make CBD-Ca and CBD-Mg with fresh $CaH_2$ and $MgH_2$.

Pharmacokinetics (PK) of Cannabidiol (CBD)-choline (Ch) salt: Comparison of the CBD PK profile following administrations of CBD and the Ch-CBD salt to freely moving rats.

Formulation Properties

CBD and the CBD-choline salt were dissolved in the mixture of lipids and surfactants shown in Table 3. And dispersed in water to form a nano dispersion of about 30 nanometer. This dispersion was administered to rats by either IV or orally.

TABLE 3

PNL formulation used to disperse CBD and its salts in aqueous media.

| Excipient | % (w/w) |
|---|---|
| Tween 20 | 14.1 |
| Span 80 | 14.1 |
| Lecithin | 8.3 |
| Tricaprin | 14.1 |

TABLE 3-continued

| PNL formulation used to disperse CBD and its salts in aqueous media. | |
|---|---|
| Excipient | % (w/w) |
| Hydrogenated castor oil (HCO 40) | 14.1 |
| Ethyl lactate | 35.4 |
| SUM | 100 |

For IV administration: Each molecule was dissolved (2% w/w) in pro-nano lipospheres (PNL) formulation (Table 3). Double-distilled water (DDW) was added to a final CBD concentration of 0.2% w/w in the nano-suspension.

For oral administration: Each molecule was dissolved (5% w/w) in pro-nano lipospheres (PNL) formulation (Table 2). Double-distilled water (DDW) was added to a final CBD concentration of 0.5% w/w in the nano-suspension.

The percentages above refer to the actual weight amount of the salts, the correction for this amount is mentioned at Table 4 and 5, below:

TABLE 4

Dosage adjustments by Mw difference ratio

| | MW | Ratio | Administration | % in PNL | % in suspension | Dose (mg/kg) |
|---|---|---|---|---|---|---|
| CBD | 314.5 | — | IV | 2 | 0.2 | 1 |
| | | | PO | 5 | 0.5 | 15 |
| Ch-CBD | 520.8 | 0.60 | IV | 1.21 | 0.12 | 0.60 |
| | | | PO | 3.02 | 0.30 | 9.06 |

TABLE 5

Correction factor and dosage adjustments by MS characterization

| | Ratio | Administration | % in PNL | % in suspension | Dose (mg/kg) |
|---|---|---|---|---|---|
| CBD | — | IV | 2 | 0.2 | 1 |
| | | PO | 5 | 0.5 | 15 |
| Ch-CBD | 0.17 | IV | 0.34 | 0.03 | 0.17 |
| | | PO | 0.85 | 0.09 | 2.55 |

Pharmacokinetics (PK) in rats of Cannabidiol (CBD)-choline (Ch) salt following IV and oral administration: Pharmacokinetic study was performed using the freely moving rats model. For intravenously administration a dosage of 1 mg/kg was given (corrections for the salts are in Tables 4 and 5). Two groups were assigned randomly to be administered with either CBD (n=5) or Ch-CBD (n=4). Systemic blood samples (0.35 mL) were taken at 5-min pre-dose and at 5, 15 30 minutes and 1, 1.5, 2, 4, 6, and 8 hr. post dose.

The oral formulation was administered to the animals by oral gavage with a dosage of 15 mg/kg (corrections for the salts are in Tables 4 and 5). Two groups were assigned randomly to be administered with either CBD (n=5) or Ch-CBD (n=3). Systemic blood samples (0.35 mL) were taken at 5-min pre-dose and at 0.33, 0.66, 1, 1.5, 2, 4, 6, 8 and 10 hr. post dose. To prevent dehydration, equal volumes of physiological solution were administered following each withdrawal of blood sample. Plasma was separated by centrifugation (4000 rpm, 10 min) and stored at −20° C. pending analysis. Plasma aliquots of 150 μL were spiked with 10 μL of internal standard cannabigerol (CBG; 1 μg/mL). ACN (200 μL) was added to each test tube (tubes A) and vortex-mixed for 1 min. The extraction of CBD and CBG was performed by N-hexane (3 mL) that was added to each test tube (tubes A), followed by 1 min. vortex-mixing. After centrifugation at 4000 rpm for 10 min, the n-hexane organic layer was transferred to fresh glass test tubes (tubes B) and evaporated to dryness (Vacuum Evaporation System, Labconco, Kansas City, MO). Then, tubes B were reconstituted in 80 μL of ACN: water (80:20). The resulting solution (80 μl) was injected into the HPLC-MS system. Column used: XTerra MS C18 Column 3.5 μm 2.1×100 mm column (Waters®, Milford, MA). Mobile phase: an isocratic mobile phase of 20:80 (v/v) 2 mM ammonium acetate/acetonitrile. Diluent: 20:80 (v/v) water/acetonitrile. Flow rate: 0.2 mL/min. Column temperature: 35° C.±5° C. Sample Temperature: 20° C.±5° C. The detection masses (m/z): CBG—312.2 and CBD-313.2, with negative electrospray.

CBD and Ch-CBD Salt Pharmacokinetics Profiles Comparison

The amounts found in the plasma for the salts were adjusted with the 0.17 correction factor mentioned in Table 6, to resemble dosage of 1 mg/kg for IV administration and 15 mg/kg for oral administration.

TABLE 6

PK parameters of CBD following IV administration of 1 mg/kg (or adjusted to that dosage) of CBD and CBD-Choline given in PNL formulation suspended (X10) in water until 8 hours.

| Mean ± SD | CBD in PNL (n = 5) | CBD-Choline (n = 4) MW adjustment (0.6) | CBD-Choline (n = 4) MS correction (0.17) |
|---|---|---|---|
| $AUC_{0-\infty}$ (μg*hr/L) | 300 ± 43.4 | 133 ± 29.8 * | 474 ± 106 |
| Clearance (L/hr*kg) | 3.38 ± 0.43 | 7.80 ± 1.79 * | 2.19 ± 0.5 * |
| Volume of distribution (L/kg) | 7.02 ± 2.31 | 12.64 ± 3.13 * | 3.31 ± 0.84 * |
| $T_{0.5}$ (hr) | 1.45 ± 0.44 | 1.07 ± 0.05 | 0.98 ± 0.19 |

*Statistical difference found with P value < 0.05,
$AUC_{0-\infty}$ is calculated for infinity by using the terminal slope Statistical difference was found between the AUC, CL and Volume of distribution with both correction factors, using T test with P value of (0.05 while comparing each salt parameter to the CBD itself.

TABLE 7

PK parameters of CBD following PO administration of 15 mg/kg (or adjusted to that dosage) of CBD and CBD-Choline given in PNL formulation suspended (X10) in water until 10 hours.

| Mean ± SD | CBD in PNL (n = 5) | CBD-Choline (n = 3) MW adjustment (0.6) | CBD-Choline (n = 3) Ms correction (0.17) |
|---|---|---|---|
| $AUC_{0-10}$ (ng*hr/ml) | 841 ± 319 | 506 ± 290 | 1797 ± 1031 |
| $AUC_{0-\infty}$ # (ng*hr/ml) | 846 ± 321 | 517 ± 301 | 1836 ± 1070 |
| Cmax (ng/ml) | 200 ± 79.5 | 119 ± 71.9 | 423 ± 255 |
| $T_{0.5}$ (hr) | 1.05 ± 0.46 | 1.37 ± 0.47 | 1.37 ± 0.47 |
| Fabs (%) (Absolute bioavailability) | 18.8 ± 7.1 | 11.5 ± 6.7 | 40.8 ± 23.8 |
| $F_{rel}$ (%) (Relative bioavailability) | | 61 | 217 |

*Statistical difference found with P value < 0.05,
$AUC_{0-\infty}$ is calculated for infinity by using the terminal slope,
$ Fabs = % of absolute bioavailability was calculated using data of CBD in PNL by IV administration No statistical difference was found, using T test with P value of <0.05. The comparison between the CBD and Ch-CBD salt, after correcting the real amount of CBD to the Ch-CBD salt (both by MW and by MS). CBD and CBD-choline salt blood levels after IV were comparable, however, the oral bioavailability of the choline salt was significantly higher.

Example 10: Synthesis of Sodium Salt of Oxybenzone and Octyl Salicylate Sunscreens The aim of Examples 44-49 is synthesis, characterization and analysis of sodium and choline salts of oxybenzone and octyl salicylate. Oxybenzone (Sigma-Aldrich, USA) and Octyl salicylate (Sigma-Aldrich, USA) were used as received. $^1H$ NMR spectra were obtained on a Varian 300 MHz NMR spectrometer using DMSO-$d_6$ as solvent.

In a 100 mL round bottom flask, 500 mg of oxybenzone (2.19 mmol) was dissolved in 10 ml of $CH_3OH$ under nitrogen atmosphere. Then, 87.6 mg of NaOH (2.19 mmol), dissolved in 10 ml of methyl alcohol, was dropwise added to the oxybenzone solution over a long period (1 hr). The solution was kept for staring overnight at room temperature. The methyl alcohol was then removed under vacuum and the precipitate was dried under air to get solid yellowish dust as a pure sodium salt of oxybenzone.

In a 100 mL round bottom flask, 500 mg of octyl salicylate (2.0 mmol) was dissolved in 10 ml of $CH_3OH$ under nitrogen atmosphere. Then 80 mg of NaOH (2.0 mmol), dissolved in 10 ml of methyl alcohol, was dropwise added to the octyl salicylate solution over a long period (1 hr). The solution was kept for staring overnight at room temperature. The methyl alcohol was then evaporated and the precipitate was dried under air to get solid white powder as a pure sodium salt of octyl salicylate.

The synthesized sodium salt of oxybenzone and octyl salicylate are characterized by $^1H$ NMR. The peak at 12.02 ppm corresponds to —OH groups of oxybenzone are totally vanished after treatment with NaOH. All the other remaining peaks of oxybenzone are intact in case of sodium salt of oxybenzone with some up field shifting which supports the formation of phenolate anion of oxybenzone. Similarly, in case of sodium salt of octyl salicylate, the peak at 10.60 ppm corresponds to —OH groups of octyl salicylate are totally vanished after salt formation. All the other remaining peaks of octyl salicylate are also intact in case of sodium salt of octyl salicylate with some up field shifting which supports the formation of phenolate anion of octyl salicylate.

Choline-oxybenzone/octyl salicylate salts are synthesized using oxybenzone or octyl salicylate, respectively, with choline hydroxide using the following procedure (Scheme 11).

Scheme 11
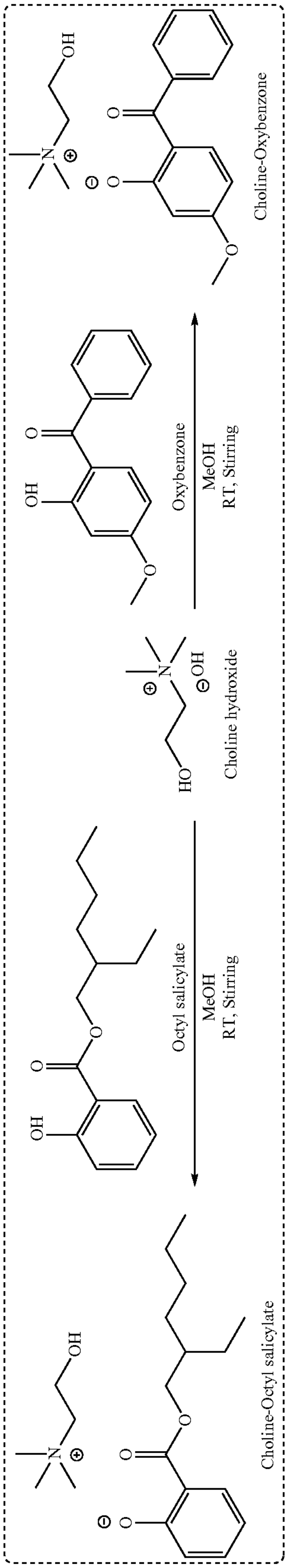

Oxybenzone/octyl salicylate (1.0 equiv.) is taken in a reaction vial with a magnetic bar. The reaction vial is kept under nitrogen atmosphere. Then methanol is added and stirred to dissolve the oxybenzone/octyl salicylate. Afterward, choline hydroxide (1.1 equiv.) solution in water is added by dropwise. Then the reaction mixture is stirred at RT. The completion of the reaction is monitored by TLC. After the completion of the reaction, methanol is removed using vacuum at RT. The resulting salt is dried using lyophilizer, which yields the choline-oxybenzone/octyl salicylate salts.

Experimental procedure: Oxybenzone (500 mg, 4.38 mmol, 1.0 equiv.) or octyl salicylate (548 mg, 4.38 mmol, 1.0 equiv.) was taken in a 20 mL reaction vial with a magnetic bar. The reaction vial was kept under nitrogen atmosphere. Then 10 mL methanol was added and stirred to dissolve the oxybenzone/octyl salicylate. Afterward, choline hydroxide solution (46% solution in water, 592 μL, 4.82 mmol, 1.1 equiv.) was added by dropwise. Then the reaction mixture was stirred at RT. After the consumption of oxybenzone/octyl salicylate, which confirmed by TLC, the methanol was removed using vacuum. The resulting product was lyophilized for overnight that yields the product as a viscous liquid (choline-oxybenzone—pale brown color clear viscous liquid; choline-octyl salicylate—pale yellow color clear viscous liquid), which analyzed using FT-IR, and NMR.

Results and discussion: Oxybenzone/octyl salicylate exhibit pale yellow color/colorless clear solution in methanol. After the choline hydroxide solution in water is added to this solution, when the reaction proceeds, the reaction mixture gradually changed to yellow/pale yellow color clear solution. After completion of the reaction, methanol was removed, and the product was obtained as a viscous liquid (choline-oxybenzone—pale brown color clear viscous liquid; choline-octyl salicylate—pale yellow color clear viscous liquid.

$^1$H NMR spectrum of oxybenzone, and choline-oxybenzone salt were compared. The peak at 12.03 ppm that corresponds to OH of oxybenzone is disappeared in the choline-oxybenzone salt. Furthermore, aromatic protons of oxybenzone are shifted (up-field) in choline-oxybenzone salt because of the more electron density of phenolate ion. In addition, nine protons of three methyl ($CH_3$) groups of the choline hydroxide are incorporated at the 3.59 ppm. Also, two methylene ($CH_2$) groups of the choline hydroxide are observed at the 3.73 ppm and 3.28 ppm.

Iron(III) salts of oxybenzone or 2-ethylhexyl salicylate. A solution of $FeCl_3$ (1.2 eq) in ethanol was added to a stirring mixture of oxybenzone or 2-ethylhexyl salicylate (1.0 eq.) in ethanol. A violet colour was visible immediately. The mixture was covered with aluminum foil and left to stir overnight at rt. Solvents were evaporated, and the crude product was taken up in chloroform and dripped into hexane. The cloudy mixture was then centrifuged and the supernatant was evaporated to afford a powder with a purple colour in quantitative yield.

Example 11: Synthesis of Salcaprozate Sodium (SNAC) Salts

Salcaprozate Sodium is the carboxylate sodium salt form of salcaprozate, an oral absorption promoter. Salcaprozate sodium is used as a delivery agent to promote the oral absorption of vitamin B, insulin, heparin and recently, semaglutide. In this example, metal and ammonium phenolate salts have been prepared with the objective to improve the formulation and improve oral bioavailability. Phenolate salts of sodium, potassium, calcium and iron were prepared using one of the methods described above. Ammonium salts with choline and tetraethylammonium ions have been prepared using methods described above. These salts have been used for the improved oral bioavailability of semaglutide and insulin.

Presented below is a chemical structure of SNAC salts. 1-SNAC; 2-SNAC-sodium; 3-SNAC-Choline, 4-SNAC-Phosphatidyl Choline.

1

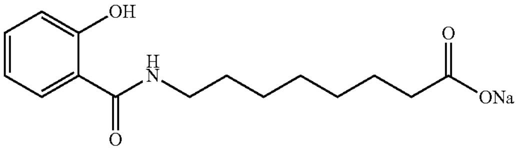

SNAC

2

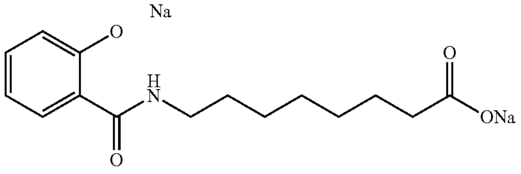

SNAC-Na

3

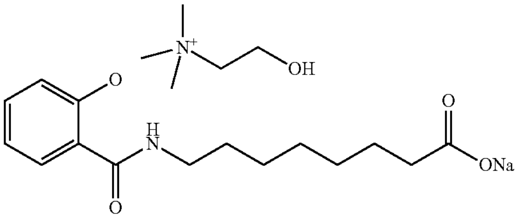

SNAC-Choline

-continued

4

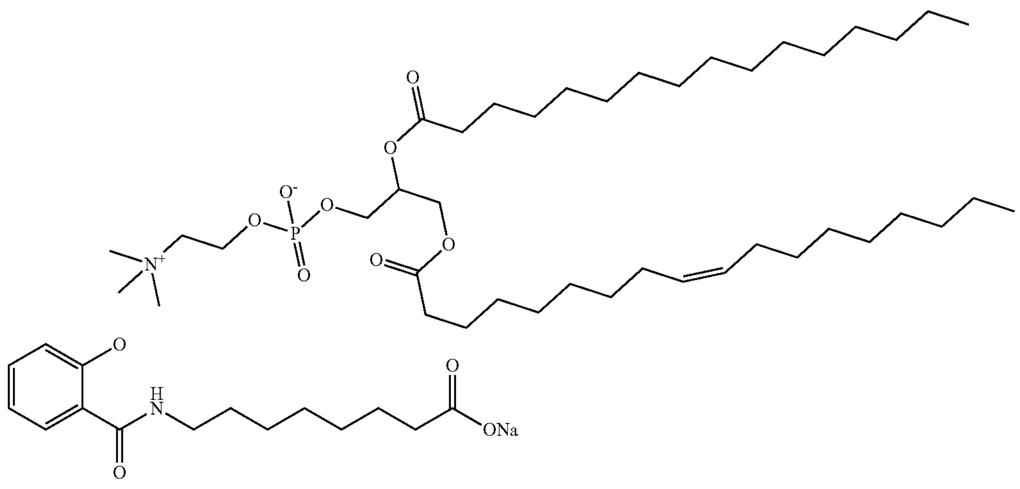

SNAC-PC

Formulation preparation: the formulations were prepared by gradual mixing of the components presented in Table 8 below. All compounds are powders and each material ratio is by mass.

TABLE 8 formulation's composition. All compounds are powders, and each ratio is by mass.

| Ingredient | % w/w |
|---|---|
| Semaglutide | 2.4 |
| SNAC or SNAC-salt | 70.7 |
| PVP K90 | 1.9 |
| Avicel ph101 | 23.6 |
| Magnesium Stearate | 1.4 |

In vivo study:

4 male Wistar rats (Harlan, Israel) are used for each SNAC or salts formulation. Pharmacokinetic study protocol: Male Wistar rats (Harlan, Israel) weighing 275-300 g are kept under a 12 h light/dark cycle with free access to food (standard rat chow) and water prior to trial. Animals are anesthetized for the period of surgery. An indwelling cannula is placed in the right jugular vein of each animal for systemic blood sampling. The cannula is tunnelled beneath the skin and exteriorized at the dorsal part of the neck. After completion of the surgical procedure, the animals are transferred to individual cages to recover overnight (12-18 h). During said recovery period, food, but not water, is deprived if an oral absorption experiment is conducted. Throughout the experiments, free access to food is available 4 h post oral administration.

Animals are randomly assigned to the different experimental groups. Oral SNAC or salts formulations and dispersed in distilled water, then administrated by oral gavage (~1.2 ml for a rat to get semaglutide dose of 12 mg/kg). Systemic blood samples (0.36 ml) are obtained by intravenous cannula, placed in the jugular vein. In the case of oral administration, samples are taken at 5 minutes pre-dose and at different time points post dose, according to the pharmacokinetic profile (blood will be drawn no more than 10% of rat blood volume). To prevent dehydration, equal volumes of physiological solution are administered to the rats following each blood sampling. Plasma is separated by centrifugation (4000 rpm, 7 minutes, 4 o C) and stored at −20° C. pending analysis. Plasma samples were analyzed by a developed LC-MS method for Semaglutide.

Results:

Salt Synthesis Characterizations:

Solubility: SNAC and salts thereof are soluble in water, except SNAC-PC which is water insoluble. While reducing the pH to acidic pH (1.2) as exists in the intestinal environment, SNAC and salts are precipitated. NMR confirmed that the salts regenerated to SNAC at this condition.

Pharmacokinetic Absorption Profile:

The absorption of semaglutide in rats was examined as semaglutide concentration in rats plasma long time after oral administration of SNAC and salts formulations. PK parameters were extracted from the data in a semi-logarithmic scale. The PK parameters extracted from the plot described in Table 9. It is clearly seen that the SNAC-Na formulations didn't contribute to the semaglutide absorption, compared to SNAC, as all PK parameters presented the lower values compared to other formulations: the AUC of this formulation, the Cmax and the absolute bioavailability. SNAC-CH presented similar PK values as the original SNAC, but the absorption of semaglutide by PC salt formulation displayed the highest AUC, Cmax and bioavailability. The % F (absolute bioavailability) in all cases is very low, however, the value for SNAC-PC in higher than the others by an order of magnitude. The commercial company of oral formulation for semaglutide reported that the bioavailability of their product was 1% in dogs. Moreover, semaglutide concentration reduction in blood over time using SNAC-PC is much slower, compared to the profile with SNAC, which indicates a good potential and improved formulation for administration of semaglutide per os. The reason for the PC salt to be the formulation which exhibited the improved absorption profile may lay on the fact that PC has two lipophilic long chains which may contribute to the hydrophobicity of the formulation and the ability to penetrate through the intestinal walls into the blood stream. It is further important to mention that the formulations were prepared by mass ratios. The molecular weight of PC is larger than SNAC, so in the case of PC salt formulation, the current amount of SNAC is much lower compared to the SNAC formulation. Thus, if to increase the SNAC amount in PC-salt formulation to be equal to the original ratio, even better results may be obtained.

PK parameters of semaglutide following PO administration of 12 mg/kg of semaglutide in SNAC, SNAC-Na, SNAC-CH or SNAC-PC formulations are shown in Table 9. $AUC_{0-\infty}{}^{\#}$ was calculated for infinity by using the terminal slope. $F_{abs}{}^{\$}$=% of absolute bioavailability was calculated using data of semaglutide in SNAC formulation by IV administration as presented in Table 10.

TABLE 9

PK parameters of semaglutide following PO administration of 12 mg/kg of semaglutide in SNAC, SNAC-Na, SNAC-CH or SNAC-PC formulations

| Mean ± SD | SNAC(n = 3) | Na (n = 3) | CH (n = 3) | PC (n = 3) |
|---|---|---|---|---|
| $AUC_{0-8}$ (μg*hr/L) | 1626 ± 739 | 1039 ± 382 | 2031 ± 335 | 5083 ± 2089 |
| $AUC_{0-\infty}{}^{\#}$ (μg*hr/L) | 1904 ± 852 | 1183 ± 339 | 2281 ± 342 | 7729 ± 4140 |
| Cmax (ng/ml) | 867 ± 378 | 323 ± 126 | 494 ± 108 | 1132 ± 486 |
| $T_{0.5}$ (hr) | 3.20 ± 0.87 | 2.26 ± 1.07 | 2.62 ± 0.35 | 4.87 ± 0.98 |
| $F_{abs}{}^{\$}$ (%) (Absolute bioavailability) | 0.095 ± 0.042 | 0.059 ± 0.017 | 0.113 ± 0.02 | 0.38 ± 0.20 |

TABLE 10

PK parameters of semaglutide following IV administration of 0.043 mg/kg of semaglutide given in SNAC formulation suspended (X10) in water, over 8 hours.

| Mean ± SD | Semaglutide in SNAC IV (n = 2) |
|---|---|
| $AUC_{0-\infty}$ (μg*hr/L) | 7199 ± 2527 |
| $T_{0.5}$ (hr) | 3.91 ± 0.26 |

Example 12: Synthesis of Di and Tricholine Molecules

Choline hydroxide was found suitable for making choline phenolate salts of active phenol containing molecules. To obtain molecules having more than one ammonium moiety, choline was dimerized by forming an ether bond or forming a carbonate bond using phosgene or phosgene derivative. Choline esters of citric acid and diacids such as oxalic, malonic, sebacic, and fumaric acid have been prepared by condensation using an esterification catalyst. Esterification onto a Poly carboxylic acid molecule such as polyacrylic acid, may form a polymer with multi-choline quaternary ammonium sites that can be used for the formation of phenolate salts.

Example 13: Preparation of Microspheres and Delivery Systems

Curcumin salt with iron or calcium at a 1:1 molar ratio to form a material that can be formulated into nano and microparticles loaded with a drug or active agent for the delivery to the human or animal body or used for the controlled delivery of agriculture substances such as fertilizers and pesticides. These compounds can be used as carriers for the delivery of drugs or cosmetics to the skin.

Example 14: Preparation of Tapinarof for Treating Hidradenitis Suppurativa

Tapinarof is a phenolic molecule commonly used for treating skin disorders, particularly for hidradenitis suppurativa. This drug is delivered either by injection under the skin at the diuseased site or applied topically using an ointment or cream. The objective of this example is to prepare metal or ammonium salts of Tapinarof to increase skin penetration and/or allow extended release of this drug. Salts of silver, copper, zinc and choline were prepared as described above. The salts released the drug in aqueous media for periods from a few days to 4 weeks. The salts were formulated into ointment and cream topical carriers as well as in Lipid or PLGA microsphres for extended release after application.

Example 15: Preparation of Green Tea Polyphenol Nanoparticles

Polyphenols extracted from Green Tea, in water at a concentration of 10 mg/ml, were mixed in an aqueous solution of $FeCl_3$ at a 1:100 to 1:10 mole ratio to form nanoparticle. After 4 hours of mixing at room temperature, nanoparticles of 200-400 nanometers were obtained. The nanoparticles were isolated by lyophilization. Similarly, Ca and Zn salt nanoparticles were prepared. The factors affecting the particles size is the ratio of metal ions and the phenolic groups. Increase in the amount of metal ions per phnolic groups as well as decreasing the concentration of the phenol and metal ions in the aqueous solution decreases the size of the nanoparticles.

Similarly, nano and microparticles of tannic acid with different metal ions were prepared by dissoving the polyphenol in NaOH and to the solution, metal salts were added and mixed for 30 minutes until a nice precipitate is obtained. The particles were isolated by centrifugation or filtration to from a free flowing water insoluble nanparticles and microparticles of the phenolic molecules. Natural polyphenols and mixtures of polyphenols of different sources were used to prepare nano and microparticles with metal ions for use as controlled release systems and entrappment of drugs for controlled drug delivery or as food additives. Synthetic polydopamine was reacted with metal ions to form ionic polydopamine. The monovalent metal salys of Na, K and Li formed relatively soluble polymers while the divalent and trivalent metal ions formed insoluble materials. Insoluble salts were prepared with Ca, Mn, Mg, Zn, Cu, Al and Fe.

In additional example, ammonium salts of choline and tetrabutyl ammonium were prepared from the direct reaction with the hydroxides of the ammonium ions.

Example 16: Metal Salts of Cinnamon Extract

Water soluble cinnamon extract as described in Food Sci. Biotechnol. 24(4): 1201-1207 (2015) were reacted with sodium and potassium salts in water to form soluble phenolate salts or water insoluble cinnamon extract with Ca, Mn, Mg, Zn, Cu, Al and Fe. The preparation of the salts was as described above. High molecular weight cinnamon extracts of molecular weights in the range of 1000 to 20000 or in the form of nanoparticles were used for the preparation of metal or ammonium salts. These salts have shown antiviral and antimicrobial activity when tested against a range of microbial agents.

Example 17: Thymol (2-Isopropyl-5-Methylphenolate) Salts

The objective is the Synthesis, characterization, and regeneration studies of 2-isopropyl-5-methylphenolate-metal salts with the comparison of thymol (Scheme 11).

Scheme 11

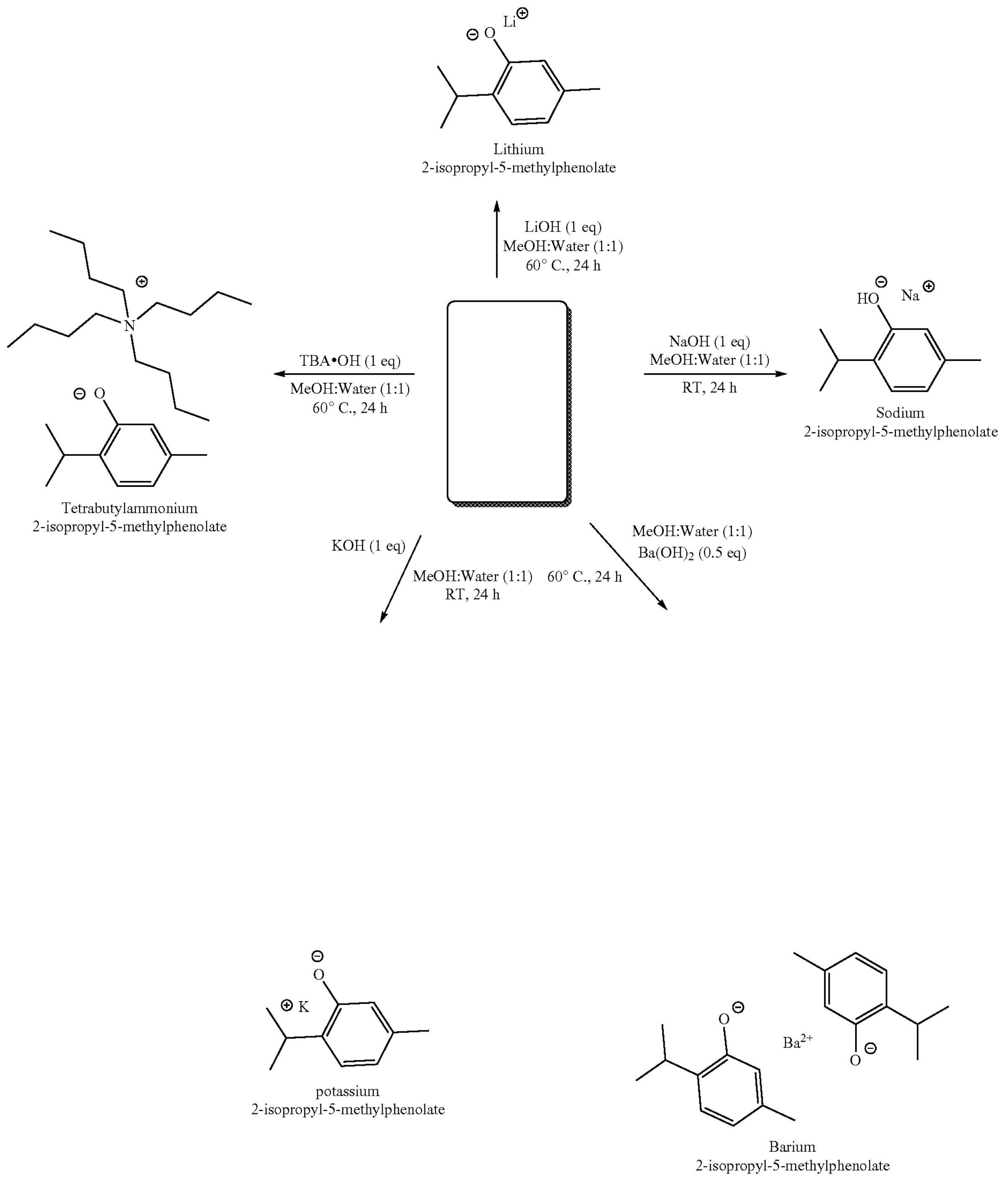

Lithium 2-isopropyl-5-methylphenolate

Tetrabutylammonium 2-isopropyl-5-methylphenolate

Sodium 2-isopropyl-5-methylphenolate potassium 2-isopropyl-5-methylphenolate

Barium 2-isopropyl-5-methylphenolate

The K, Li, Na and Ba salts of thymol were synthesized by reacting thymol with its corresponding alkali metal hydroxides i.e. KOH, LiOH, NaOH, and $Ba(OH)_2$ in the presence of water/methanol mixture at RT or 60° C. for 24 h respectively. Similarly, the tetrabutylammonium 2-isopropyl-5-methylphenolate was prepared by reacting an equimolar amount of thymol with tetrabutylammonium hydroxide (TBA.OH) in the presence of water/methanol mixture at 70° C. for 24 h (See Scheme 11). While Cu, Zn, Fe, and Mn salts of thymol were prepared by stirring sodium 2-isopropyl-5-methylphenolate with the corresponding transition metal sulfate/chlorides $CuSO_4$, $ZnCl_2$, $FeCl_2$, and $MnCl_2$ in the presence of water at RT for 24 h respectively (See Scheme 12). All the synthesized thymol-salts were thoroughly characterized by using various analytical and spectroscopic techniques including NMR, IR, UV-Visible, DSC, EDX, and elemental analysis.

Scheme 12

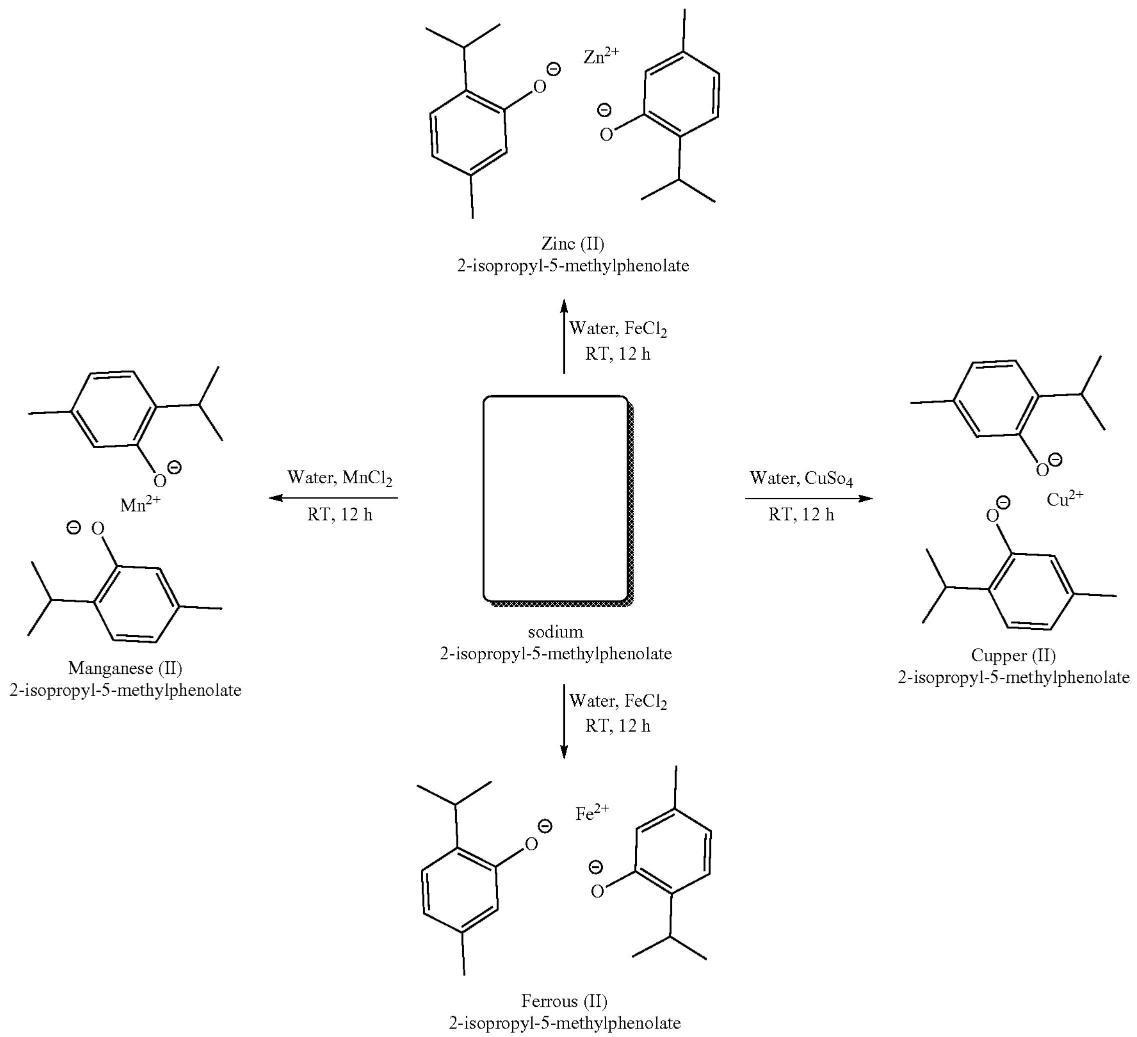

Zinc (II) 2-isopropyl-5-methylphenolate

Manganese (II) 2-isopropyl-5-methylphenolate sodium 2-isopropyl-5-methylphenolate Cupper (II) 2-isopropyl-5-methylphenolate Ferrous (II) 2-isopropyl-5-methylphenolate The syntheses and characterization details of various 2-isopropyl-5-methylphenolate-metal salts were described is as follows:

Synthesis of potassium 2-isopropyl-5-methylphenolate: Thymol (1 gm, 6.656 mmol) dissolved in 5 mL MeOH was added drop-wise to KOH (0.373 gm, 6.656 mmol) in 4 mL of water. Afterward, the reaction mixture was stirred at RT for 24 h. After completion of the reaction, the reaction mixture was evaporated under rota vapor. The resultant black sticky solid was washed with n-heptane (10 mL×3) and dried in a hot air oven at 50° C. for 24 h. Yield: 60% (0.760 gm) FT-IR: vmax/$cm^{-1}$ 2956-2865 (v C—H stretching), 1589-1556-1487-1447-1397 (v C═C stretching), 1292-1270-1242-1193-1165-1150 (v C—O stretching), 1111, 1085-1056-1006 (v C—H in plane bending), 951 (v C═C bending), 857-794-738 (v C—H out plane bending) $cm^{-1}$. $^1$H-NMR (300 MHz, DMSO-$d_6$): δ=6.57 (d, 1H, J=9 Hz, Ar—H), 6.02 (s, 1H, Ar—H), 5.76(d, 1H, J=6 Hz, Ar—H), 3.25-3.16 (m, 1H, iPr-H), 1.98 (s, 3H, Ar—$CH_3$), 1.01 (d, 6H, J=9 Hz, iPr—$(CH_3)_2$).

Synthesis of lithium 2-isopropyl-5-methylphenolate: Thymol (1 gm, 6.656 mmol) dissolved in 6 mL MeOH was added drop-wise to LiOH (0.279 gm, 6.656 mmol) in 6 mL of water. Afterward, the reaction mixture was stirred at 70° C. for 24 h. After completion of the reaction, the reaction mixture was evaporated under rota vapor. The resultant dark brown precipitate was washed several time with water (10 mL×3) and n-heptane (10 mL×3) and dried in a temperature-controlled hot air oven at 50° C. for 24 h. Yield: 87% (0.900 gm). FT-IR: vmax/$cm^{-1}$2957-2922 (v C—H aromatic), 2865 (v C—H aliphatic), 1596-1577-1562-1508-1447-1401 (v C═C), 1292-1274-1233-1169-1157-1112 (v C—O), 1086-1054-1037-1000 (v C—H in plane bending), 953-946 (v C═C bending), 867-859-803-745 (v C—H out plane bending) $cm^{-1}$. $^1$H-NMR (300 MHz, DMSO-$d_6$): δ=6.69 (d, 1H, J=6 Hz, Ar—H), 6.31 (s, 1H, Ar—H), 5.97(d, 1H, J=6 Hz, Ar—H), 3.48-3.26 (m, 1H, iPr-H), 2.03 (s, 3H, Ar—$CH_3$), 1.06 (d, 6H, J=6 Hz, iPr—$(CH_3)_2$).

Synthesis of tetrabutylammonium 2-isopropyl-5-methylphenolate: Thymol (1.00 gm, 6.65 mmol) dissolved in 5 mL MeOH was added drop-wise to TBA.OH.30 $H_2O$ (5.32 gm, 6.65 mmol) in 5 mL of water. Afterward, the reaction mixture was stirred at 50° C. for 24 h. After completion of the reaction, the reaction mixture was evaporated under rota vapor. The resultant sticky solid gave wheat color precipitates upon addition of the distilled water (40 mL), which was further collected using Buchner funnel and washed subsequently several times with distilled water (40 mL×3) and n-heptane (20 mL×3) followed by drying in a temperature-controlled hot air oven at 50° C. for 24 h. Yield: 1.20 gm (46%). $^1$H-NMR (300 MHz, DMSO-$d_6$): δ=6.79 (d, 2H, J=6 Hz, ArH), 6.51 (s, 2H, ArH), 6.21 (d, 2H, J=6 Hz, ArH), 3.27-3.20 (m, 2H, iPr-H), 3.18-3.13 (m, 8H, TBA), 2.06 (s, 3H, Ar—$CH_3$), 1.61-1.51 (m, 8H, TBA),1.36-1.24 (m, 8H, TBA), 1.11-1.09 (m, 6H, iPr—$(CH_3)_2$), 0.95-0.91 (m, 12H, TBA). FT-IR: vmax/$cm^{-1}$ 2960 (v C—H aromatic), 2872 (v C—H aliphatic), 1586-1480-1458-1380 (v C═C), 1283-1235-1148 (v C—O), 1087-1050-1004 (v C—H in plane bending), 948 (v C═C bending), 883-864-798-738 (v C—H out plane bending) $cm^{-1}$.

Synthesis of sodium 2-isopropyl-5-methylphenolate: Thymol (20 gm, 133.13 mmol) dissolved in 30 mL MeOH was added drop-wise to NaOH (5.857 gm, 146.451 mmol) in 40 mL of water. Afterward, the reaction mixture was stirred at RT for 24 h. After completion of the reaction, the reaction mixture was evaporated under rota vapor. The resultant black sticky solid was washed several time with n-heptane (50 mL×3) and then dried in a hot air oven at 50° C. for 24 h. FT-IR: vmax/$cm^{-1}$ 2952 (v C—H aromatic), 2864 (v C—H aliphatic), 1635-1595-1557-1491-1396 (v C═C), 1289-1263-1196-1166-1151 (v C—O), 1086-1054-1008 (v C—H in plane bending), 952 (v C═C bending), 860-795-739 (v C—H out plane bending) $cm^{-1}$. $^1$H-NMR (300 MHz, DMSO-$d_6$): δ=6.66 (d, 1H, J=6 Hz, Ar—H), 6.22 (s, 1H, Ar—H), 5.93(d, 1H, J=9 Hz, Ar—H), 3.25-3.16 (m, 1H, iPr-H), 2.00 (s, 3H, Ar—$CH_3$), 1.05 (d, 6H, J=9 Hz, iPr—$(CH_3)_2$).

Synthesis of 2Na(2-isopropyl-5-methylphenolate)$_4$Zn: Na-Thymol (5 gm, 29.03 mmol) dissolved in 70 mL of dry THF was added drop-wise to Zn(II)$Cl_2$ (1.009 gm, 7.404 mmol) in 20 mL of dry THF. Afterward, the reaction mixture was allowed for stirring at RT for 36 h. After completion of the reaction, the NaCl was removed from the reaction mixture by centrifugation. Thereafter, the resultant clear solution was evaporated under reduced pressure followed by drying in a hot air oven at 50° C. for 24 h. Yield: 71% (3.742 gm) FT-IR: vmax/$cm^{-1}$ 2959 (v C—H aromatic), 2868 (v C—H aliphatic), 1581-1506-1493-1456-1418 (v C═C), 1287-1230-1181-1152 (v C—O), 1087-1058 (v C—H in plane bending), 945 (v C═C bending), 861-805-738 (v C—H out plane bending) $cm^{-1}$. $^1$H-NMR (300 MHz, DMSO-$d_6$): δ=6.93 (d, 1H, J=6 Hz, Ar—H), 6.57 (s, 1H, Ar—H), 6.48(d, 1H, J=9 Hz, Ar—H), 3.22-3.08 (m, 1H, iPr-H), 2.14 (s, 3H, Ar—$CH_3$), 1.11 (d, 6H, J=9 Hz, iPr—$(CH_3)_2$).

The resultant structure is as follows:

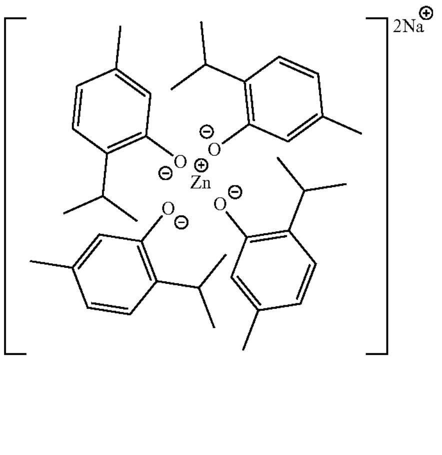

Synthesis of barium 2-isopropyl-5-methylphenolate: Thymol (0.5 gm, 3.28 mmol) dissolved in 5 mL MeOH was added drop-wise to $Ba(OH)_2$·$8H_2O$ (0.5 gm, 1.64 mmol) in 10 mL of water. Afterward, the reaction mixture was allowed for stirring at 70° C. for 24 h. After completion of the reaction, the reaction mixture was evaporated under rota vapor. The resultant black precipitate was washed several times with n-heptane (10 mL×3) and dried in a hot air oven at 50° C. for 24 h. Yield: 0.520 gm (36%). FT-IR: vmax/$cm^{-1}$ 2961 (v C—H aromatic), 2872 (v C—H aliphatic), 1578-1423 (v C═C), 1290-1246-1177 (v C—O), 1089-1059 (v C—H in plane bending), 947 (v C═C bending), 855-807-768 (v C—H out plane bending) $cm^{-1}$. $^1$H-NMR (300 MHz, DMSO-$d_6$): δ=6.95 (d, 1H, J=9 Hz, Ar—H), 6.56 (s, 1H, Ar—H), 6.53 (d, 1H, J=9 Hz, Ar—H), 3.32-3.08 (m, 1H, iPr-H), 2.16 (s, 3H, Ar—$CH_3$), 1.11 (d, 6H, J=9 Hz, iPr—$(CH_3)_2$).

The resultant structure is as follows:

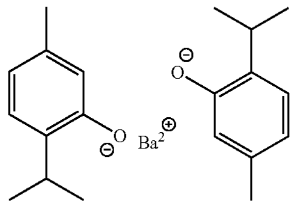

Synthesis of copper(II) 2-isopropyl-5-methylphenolate: Cu(II)$SO_4$.$5H_20$ (139.199 gm, 557.49 mmol) dissolved in 500 mL distilled water was added slowly to Na-Thymol (192 gm, 1114.9 mmol) in 1 L of distilled water. After addition, the immediate formation of green precipitate was observed. Afterward, the reaction mixture was allowed for stirring for 24 h. After completion of the reaction, the reaction mixture was filtered through the Buchner funnel followed by washing with excess distilled water (200 mL×3). The resultant greenish precipitate was dried in a temperature-controlled hot air oven at 50° C. for 24 h. Yield: 80% (160.3 gm). The compound is inactive for NMR analysis due to the paramagnetic nature of Cu(II) ion. FT-IR: vmax/$cm^{-1}$ 2958 (v C—H aromatic), 2868 (v C—H aliphatic), 1583-1491-1455-1417 (v C═C), 1338-1286-1243-1177-1155 (v C—O), 1088-1058-1004 (v C—H in plane bending), 943 (v C═C bending), 894-805-737 (v C—H out plane bending) $cm^{-1}$.

The resultant structure is as follows:

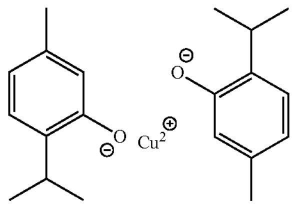

Synthesis of zinc(II) 2-isopropyl-5-methylphenolate: Zn(II)$Cl_2$ (0.451 gm, 3.31 mmol) dissolved in 5 mL distilled water was added drop-wise to Na-Thymol (1.14 gm, 6.62 mmol) in 10 mL of distilled water. After addition, the immediate formation of wheat color precipitate was observed. Afterwards, the reaction mixture was allowed for stirring at RT for 24 h. After completion of the reaction, the reaction mixture was filtered through the Buchner funnel followed by washing with excess distilled water (20 mL×3).

The resultant wheat color precipitate was dried in a temperature-controlled hot air oven at 50° C. for 24 h. Yield: 71.3% (0.85 gm). FT-IR: vmax/$cm^{-1}$ 2962 (v C—H aromatic), 2868 (v C—H aliphatic), 1551-1457-1418 (v C═C), 1289-1260-1155 (v C—O), 855-829-807 (v C—H out plane bending) $cm^{-1}$.

The resultant structure is as follows:

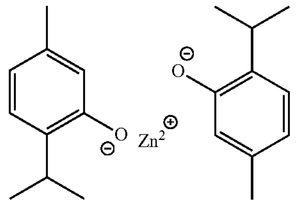

Synthesis of ferrous (II) 2-isopropyl-5-methylphenolate: Fe(II)$Cl_2$ (0.367 gm, 2.903 mmol) dissolved in 5 mL distilled water was added drop-wise to Na-Thymol (1 gm, 5.87 mmol) in 10 mL distilled water. After addition, the immediate formation of wheat color precipitate was observed. Afterward, the reaction mixture was allowed for stirring at RT for 24 h. After completion of the reaction, the reaction mixture was filtered through the Buchner funnel followed by washing with excess distilled water (20 mL×3). The resultant wheat color precipitate was dried in a temperature-controlled hot air oven at 50° C. for 24 h. Yield: 37% (0.380 gm). FT-IR: vmax/$cm^{-1}$ 2960 (v C—H aromatic), 2869 (v C—H aliphatic), 1642-1611-1599-1506-1455 (v C═C), 1288-1255-1220-1154 (v C—O), 890-855-809 (v C—H out plane bending) $cm^{-1}$.

The resultant structure is as follows:

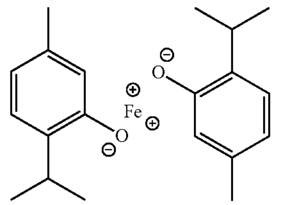

Synthesis of silver 2-isopropyl-5-methylphenolate: $AgNO_3$ (0.986 gm, 5.807 mmol) dissolved in 4 mL dry acetonitrile was added drop-wise to Na-Thymol (1 gm, 5.87 mmol) in 10 mL dry acetonitrile. Afterward, the reaction mixture was allowed for stirring at RT for 24 h. After completion of the reaction, the reaction mixture was filtered by Whatman filter paper followed and evaporated using rota vapor. The resultant solid was dried in a temperature-controlled hot air oven at 50° C. for 24 h. Yield: 55% (0.820 gm). FT-IR: vmax/$cm^{-1}$ 2961 (v C—H aromatic), 2870 (v C—H aliphatic), 1652-1537-1485-1412 (v C═C), 1289-1223-1175 (v C—O), 855-829-807 (v C—H out plane bending) $cm^{-1}$. $^1$H-NMR (300 MHz, DMSO-$d_6$): δ=7.31 (s, 1H, Ar—H), 7.13 (s, 1H, Ar—H), 6.96 (s, 1H, Ar—H), 3.18-3.10 (m, 1H, iPr-H), 1.85 (s, 3H, Ar—$CH_3$), 1.17-1.10 (m, 6H, iPr—$(CH_3)_2$).

The resultant structure is as follows:

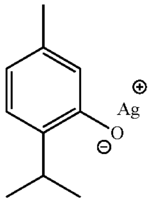

Characterization of 2-isopropyl-5-methylphenolate-salts

NMR analysis: The presence of organic units in a series of 2-isopropyl-5-methylphenolate-salts were characterized by using NMR analysis. All the samples were recorded in the deuterated DMSO-d6 at room temperature. In contrast to the thymol, the absence of aromatic hydroxyl resonances in these samples around 9 ppm shows that thymol is deprotonated and this observation reveals their salt nature. Moreover, the aromatic protons of thymol-salts were shielded compared to those in thymol, further revealing their salt nature. Cu, Fe, Mn salts of 2-isopropyl-5-methylphenolate were inactive for NMR analysis due to their paramagnetic nature.

IR Ananlysis: The FT-IR spectra of all thymol-salts were recorded with the comparison to thymol. Thymol showed FT-IR stretching frequency for the hydroxyl group at 3177.48 $cm^{-1}$ while this peak is missing in its analog thymol-salts, confirming their salt nature. However, thymol-Li and thymol-Fe showed stretching frequencies for hydroxyl groups at 3436 $cm^{-1}$ and 3387 $cm^{-1}$ respectively. The assumption is that this might be due to coordinating solvent water molecules in its molecular structure since the reaction was performed in water. The aromatic and alkyl (methyl/isopropoyl)C—H starching frequencies of these compounds showed in the range of 2922-2961 $cm^{-1}$ and 2865-2872 $cm^{-1}$ respectively. Most importantly, these compounds exhibited aromatic C═C and C—O starching frequency in the range of 1635-1418 $cm^{-1}$ and 1290-1155 $cm^{-1}$ respectively.

DSC analysis: The melting temperature of various thymol-salts was determined with the comparison to thymol using Differential Scanning Calorimetry (DSC). DSC studies reveal that thymol-salts showing different melting temperature than the parent thymol (See Table 11).

TABLE 11

Melting temperature and enthalpy of various thymol-metal salts with the comparison to thymol.

| Thymol Salt | Melting temperature (° C.) | Enthalphy (Jg-1) |
|---|---|---|
| Thymol | 50.38 | 197.17 |
| Lithium | 111 | −45.72 |
| Silver | 209.01 | −40.41 |
| Barium | 67.61 | −27.83 |
| Cupper (II) | 178.01 | −94.34 |
| | 211.06 | −16.42 |
| Ferrous (II) | 50.92 | −194.68 |
| | 203.22 | −439.36 |
| Sodium | 38.18 | −69.65 |
| Tetrabutylammonium | 110.54 | −59.90 |
| Zinc (II) | 51.88 | −111.64 |
| | 171.55 | −338.25 |

UV-Visible spectroscopy: In order to study the electronic transitions, various 2-isopropyl-5-methylphenolate-salts were subjected for UV-Visible analysis with the comparison to thymol in DMF at diluted concentrations. The results reveal that the absorption of Zn, Co, Li, Fe, Ba, and Ag salts of 2-isopropyl-5-methylphenolate are blue-shifted. While the absorptions TBA, Mn, and Cu salts of 2-isopropyl-5-methylphenolate are within the range of thymol. The absorption of various thymol salts with the comparison to thymol described as follows: thymol: 277, 283 nm; Zinc (II) 2-isopropyl-5-methylphenolate: 266 nm; cobalt (II) 2-isopropyl-5-methylphenolate: 265 nm; lithium 2-isopropyl-5-methylphenolate: 269 nm; ferrous (II) 2-isopropyl-5-methylphenolate: 264 nm; tetrabutylammonium 2-isopropyl-5-methylphenolate: 277, 283 nm; manganese (II) 2-isopropyl-5-methylphenolate: 282; copper (II) 2-isopropyl-5-methylphenolate: 282 nm; barium 2-isopropyl-5-methylphenolate: 268 nm; silver 2-isopropyl-5-methylphenolate: 268 nm; 2Na(2-isopropyl-5-methylphenolate)$_4$ Zn: 277,282 nm. The analyses clearly demonstrate the presence of thymol in the 2-isopropyl-5-methylphenolate-salts.

EDX analysis: EDX analysis was conducted for 2-isopropyl-5-methylphenolate-metal salts in order to identify the percent composition of metal ions therein. The presence of different metals including Ag, Na, K, Fe, Zn, Fe, and Mn with different atomic and weight compositions confirming the formation of their corresponding-isopropyl-5-methylphenolate-metal salt.

Regeneration of thymol from 2-isopropyl-5-methylphenolate-metal salts in acidic aqueous media Experimental procedure for regeneration studies: Regeneration studies were performed for 2-isopropyl-5-methylphenolate-salts in the 0.1 N HCl solution (1 pH) followed by extracting free thymol with heptane. The appropriate amount of the corresponding thymol-salt (Table 12) was brought into the 20 mL glass vial. To this, 10 mL of 0.1 N was added. The resultant mixture was kept in a shaker for 30 min. After 30 min of acid treatment, 10 mL of heptane was added to the reaction mixture. The collected organic layer was separated from the water layer and carefully dried using rotavapor followed by drying under a temperature-controlled hot oven at 35° C. for 12 h. The percentage of the thymol regenerated after the acid treatment of various thymol-salts is presented in Table 12.

TABLE 12

Regeneration studies of thymol from thymol-salts in the 0.1N HCl solution (pH = 1).

| Characterization of regenerated Thymol | | | | |
|---|---|---|---|---|
| Thymol salt | weight taken | Thymol regenerated | thymol regenerated (theoretical yield) | % of thymol regenerated |
| Sodium | 105 mg | 62.39 mg | 90.9 mg | 68 |
| Tetrabutylammonium | 75.2 mg | 27.02 mg | 28.62 mg | 94 |
| Copper (II) | 126.21 mg | 74.63 mg | 103.974 mg | 72 |
| Zinc (II) | 112.64 mg | 54.52 mg | 92.38 mg | 59 |
| Ferrous (II) | 127.64 mg | 103.9 mg | 107.51 mg | 97 |
| Manganese(II) | 56.58 mg | 36.95 mg | 47.78 mg | 77 |
| Silver | 61.43 mg | 20.32 mg | 35.62 mg | 57 |
| Lithium | 129.80 mg | 77.12 mg | 123.9 mg | 63 |
| $2Na_4Zn$ | 102.01 mg | 63.84 mg | 86.127 | 74 |
| Potassium | 49.71 mg | 22.5 mg | 39.35 mg | 57 |

The regenerated thymol was characterized by using NMR and IR analysis. The characterization data reveals that all the synthesized thymol-salts are having the ability to convert back to thymol after acid treatment. For example, the regenerated thymol obtained from TBA-isopropyl-5-methylphenolate was shown resonance at 9.06 ppm, which corresponds to an aromatic hydroxyl group. This indicates the conversion of TBA-isopropyl-5-methylphenolate to thymol and TBA-Cl in the acidic aqueous media.

In addition, missing TBA resonances in the same spectra confirms the regeneration of thymol back from TBA isopropyl-5-methylphenolate. Similarly, sodium-isopropyl-5-methylphenolate also confirms the regeneration of thymol by exhibiting hydroxyl resonance at 9.06 ppm after the acid treatment. Moreover, the FT-IR spectra of the regenerated thymol shows the stretching frequency for the aromatic hydroxyl group at 3424 $cm^{-1}$ which further confirms the regeneration of thymol back from sodium-isopropyl-5-methylphenolate.

Solubility Studies

The solubility studies of various thymol-salts were performed in the different aqueous pH solutions (pH=4, 7, and 10) and organic solvents including ethanol, acetone, and propyleneglycol. The salts were insoluble in water at any pH, except of the sodium salt that was soluble in water. Some salts had some solubiility in organic solvents.

Summarization of the Above Experiments

Na, K, TBA, Mn, Fe, Ag, Cu Li, Ba, and Zn salts of thymol have been prepared with the comparison to parent thymol molecule and analyzed. The formation of the corresponding salts was confirmed by the missing hydroxyl resonances for the salts around 9 ppm in the $^1$H-NMR spectra. The absence of FT-IR stretching frequencies in all of these compounds at 3177.48 $cm^{-1}$ compared to thymol, further confirms their salt nature. DSC studies reveal that these samples are having high melting temperature compared to thymol. The regeneration of thymol from isopropyl-5-methylphenolate-salts was studied in the acid aqueous media (pH=1) and the characterization studies reveal the regeneration of thymol back from all samples in its pure form. The melting point of phenolate salts is higher than the original phenol, which allows processing the salt at high temperature with plastic extrusion or steam foaming.

Example 18: Antimicrobial Activity of Phenolate Salts phenolate salts demonstrates an activity in protecting crops from bacterial and fungal infections. The following materials were tested: copper salicylate, salicylic acid, copper thymol and thymol.

The materials were tested against the following contaminants: *Erwinia* (bacteria), *Pythium* (fungi), *Macrophomina Phaseolina* (fungi), *Athelia Rolfsii* (fungi) and Potato Scab (bacteria).

Roots infected with the above pathogens were collected and decontamination was performed. *Erwinia* infected roots were exposed to two tests. In the first test, the percentage of rotten potatoes was measured after 30 days. In the second test, the crop yield after 120 days was measured.

Lab tests were performed against *Erwinia, Pythium, Macrophomina phaseolina* and *Athelia rolfsii*

Potato scabs were evaluated in crops after 110 days of growing in spring 2020.

Both the level of scabbing and the crop yield were measured.

*Pythium* was further evaluated in a field test in spring 2020. *Pythium* levels were measured after 110 days of growing.

Results

Both *Erwinia* and scabs were eradicated under laboratory conditions with all agents Copper salicylate was the most active compound against *Pythium* infections.

Copper salicylate showed improved activity relative to salicylic acid.

Activity was greater against *Macrophomina Phaseolina* than other fungi

The copper and zinc-thymol salts were incorporated in polystyrene foam, in a hydrogel during their manufacturing and in coating material of potato seeds and hay packaging material. Moreover, the thymol copper was incorporated in polyethylene sheets during melt extrusion. The salts were incorporated in these formulations while thymol could not be incorporated due to its evaporation rate and low melting point. Thymol was constantly released to air over a period of 3 weeks while protecting the hay from microbial contamination.

In a typical experiment, fresh hay was packed with thymol coated and copper-thymol salt coated packaging. After 2 weeks, the control bale became moldy. The coated bale has not shown any mold.

Example 19: Release of Salicylic/Benzoic Acid from Polystyrene Foam which Contains 6% Cu-Salicylic/Benzoic Acid Copper salicylate, copper benzoate and mixtures thereof were prepared as described in the above examples. Due to the high melting point and water insolubility, these salts were able to be efficiently incorporated into polystyrene foams during steam blowing. Polystyrene foam trays containing 6% Cu-Salicylic acid or 6% Cu-Benzoic acid were investigated for their salicylic/benzoic acid release properties. The release study was done in DDW at room temperature with a shaking of 150 rpm. Around 10 g of foam samples were taken for each tray and added to 550 mL of DDW until total immersion. Polystyrene foam without any active agent was employed as a reference. The solution was replaced after 1 h, and 1, 2, 8, 16 and 30 days. The solutions were analyzed for salicylic/benzoic acid quantity using UV by measuring the absorption at 298 nm and 225 nm respectively. Lyophilization process was performed where the detectable concentration is very low. Polystyrene foam trays containing 6% Cu-Salicylic acid showed salicylic acid release of 34.5 mg per tray in 30 days and the 6% Cu-Benzoic acid demonstrated benzoic acid release of 30.7 mg per tray in 30 days. The release profile of salicylic/benzoic acid from the polystyrene foam is presented in the below Table 13.

TABLE 13

Release of Salicylic/Benzoic acid from polystyrene foam containing 6% Cu-Salicylic/Benzoic acid (Release in mg per tray)

| Time (days) | Salicylic acid released from PS Foam (6% Cu-Salicylic acid) in mg per tray | Benzoic acid released from PS Foam tray (6% Cu-Benzoic acid) in mg per tray |
|---|---|---|
| 1 | 25.3 | 20.7 |
| 2 | 27.1 | 21.3 |
| 8 | 29.4 | 24.1 |
| 16 | 31.4 | 27.4 |
| 30 | 34.5 | 30.7 |

Determination of distribution of active agents in the entire polystyrene foams: During foam preparation, it is possible that heterogeneous distribution of active agents occurs in the final product due to insolubility issues. The approach herein is to analyze the distribution of the active agents in the foams.

Small parts from several sections of the tray were taken and dispersed in a water. Salicylic acid (SA) and benzoic acid was analyzed using UV absorbance spectroscopy. The metal ion, in this case Cu (II) was analyzed using ZINCON.

Small pieces were taken out from various sections of the sample foam and added to aqueous solution which strongly agitated for 24 hours. Thereafter, the solution was analyzed using UV at 296 nm for salicylic acid content. Further, the solution was diluted using ZINCON aqueous solution and analyzed by using UV absorbance at 620 nm. Similar concentration was obtained for all samples which indicate an even distribution in the foam.

The results revealed that both the active agents, Cu-SA and Cu-benzoate are uniformly distributed in the polystyrene foams.

These trays were used for planting tomato plants contaminated with various viruses. The plants in trays that contained copper salicylate or benzoate grew well and did not demonstrate any infection of contamination. On the other hand, plants in the blank polystyrene trays were heavily infected.

The invention claimed is:

1. An isolated material comprising at least one phenol-containing active material comprising at least one phenolate group and a phosphonium or an ammonium salt counter-ion, wherein the active material is not phenol ($C_6H_6O$), methylphenol, bromophenol, dibromophenol, tribromophenol, pentachlorophenol, bisphenol A, tetrabromobisphenol A, resorcinol, hydroquinone, hydroquinone or naphthol.

2. The material according to claim 1, comprising two or more of said phenol-containing active materials, each active material having one or more phenolate groups, each of the phenolate groups being associated with a different cation selected from a metal cation, a phosphonium cation and an ammonium cation.

3. The material according to claim 2, wherein the two or more phenol-containing active materials are the same or different.

4. The material according to claim 1, comprising a trivalent metal and three same or different phenol-containing active materials.

5. The material according to claim 1, comprising one or more phenol-containing active material and one or more non-active phenol-containing material.

6. An isolated material comprising at least one phenol-containing active material comprising at least one phenolate group and a metal salt, a phosphonium or an ammonium salt counter-ion, wherein the phenol-containing active material is selected from cannabinoids, fenoldopam, tyrosine, xylenol, thymol, propofol, apomorphine, morphine and derivatives thereof, mitoxantrone, dexorubicine, hexachlorophene, acetaminophen, p-coumaric acid, 3,4-dihydroxybenzoic acid, 4-hydroxybenzoic acid, butylparaben, vanillic acid, guaiacol, caffeic acid, tolterodine, raloxifea, scopoletin, decursinol, dopamine, L-DOPA, curcumin, tianine and polyphenols.

7. The material according to claim 6, wherein the phenol-containing active material is a cannabinoid material.

8. The material according to claim 7, wherein the cannabinoid is THC or CBD and chemical derivatives thereof.

9. A material comprising at least one cannabinoid in a form of a phenolate and a cation selected from metal cations, phosphonium and ammonium.

10. A calcium CBD salt comprising one CDB and optionally another non-cannabinoid or two CBDs.

11. A material being a cholate salt of at least one phenol-containing active material.

12. The material according to claim 11, wherein the at least one phenol-containing active material is a cannabinoid material.

13. A formulation selected from a pharmaceutical, cosmetic, veterinary or agricultural formulation, the formulation comprising an isolated material according to claim 1.

14. A material according to claim 1, being in the form of a multimolecular material comprising two or more phenol-containing active materials, each being ionically associated with a cation; wherein the cation is a multivalent metal cation or a poly-ammonium.

15. A particle comprising a material according to claim 1.

16. A composition or a formulation comprising a material, wherein the material comprising an ammonium cation or a poly-ammonium, and at least one active material comprising at least one phenolate moiety ionically bonded to the ammonium or the poly-ammonium cation, wherein the composition or the formulation is for use in treating a disease or disorder which is treatable by administering to a subject a therapeutically effective amount of the composition or the formulation.

17. A formulation selected from a pharmaceutical, cosmetic, veterinary or agricultural formulation, the formulation comprising an isolated material according to claim 6.

18. A material according to claim 6, being in the form of a multimolecular material comprising two or more phenol-containing active materials, each being ionically associated with a cation; wherein the cation is a multivalent metal cation or a poly-ammonium.

19. A salcaprozate sodium (SNAC) selected from choline salcaprozate sodium (SNAC-choline) and phosphatidylcholine salcaprozate sodium (SNAC-PS).

20. A material for improving oral bioavailability of semaglutide or insulin, the material being a SNAC according to claim 19.

21. A particle comprising a material according to claim 6.

* * * * *